United States Patent
Johnson et al.

(10) Patent No.: US 11,684,304 B2
(45) Date of Patent: Jun. 27, 2023

(54) NON-INVASIVE SYSTEMS AND METHODS FOR THE DETECTION AND MODULATION OF A USER'S MENTAL STATE THROUGH AWARENESS OF PRIMING EFFECTS

(71) Applicant: HI LLC, Los Angeles, CA (US)

(72) Inventors: Bryan Johnson, Culver City, CA (US); Husam Katnani, Braintree, MA (US)

(73) Assignee: HI LLC, Los Angeles, CA (US)

( * ) Notice: Subject to any disclaimer, the term of this patent is extended or adjusted under 35 U.S.C. 154(b) by 425 days.

(21) Appl. No.: 16/885,596

(22) Filed: May 28, 2020

(65) Prior Publication Data

US 2020/0390358 A1 Dec. 17, 2020

Related U.S. Application Data

(60) Provisional application No. 62/891,128, filed on Aug. 23, 2019, provisional application No. 62/859,880, filed on Jun. 11, 2019.

(51) Int. Cl.
*A61B 5/375* (2021.01)
*A61M 21/02* (2006.01)
(Continued)

(52) U.S. Cl.
CPC .......... *A61B 5/375* (2021.01); *A61B 5/0036* (2018.08); *A61B 5/0082* (2013.01); *A61B 5/165* (2013.01);
(Continued)

(58) Field of Classification Search
CPC . A61B 2503/12; A61B 5/0036; A61B 5/0059; A61B 5/0082; A61B 5/05;
(Continued)

(56) References Cited

U.S. PATENT DOCUMENTS

| | | |
|---|---|---|
| 5,377,100 A | 12/1994 | Pope et al. |
| 5,720,619 A | 2/1998 | Fisslinger |

(Continued)

FOREIGN PATENT DOCUMENTS

| | | |
|---|---|---|
| WO | WO02043564 | 6/2002 |
| WO | WO2012135068 | 10/2012 |

(Continued)

OTHER PUBLICATIONS

PCT International Search Report and Written Opinion for International Appln. No. PCT/US2020/034831, Applicant HI LLC, forms PCT/ISA/210 and 237 dated Feb. 8, 2021 (18 pages).

(Continued)

*Primary Examiner* — Thaddeus B Cox
*Assistant Examiner* — Marc D. Honrath
(74) *Attorney, Agent, or Firm* — Michael J Bolan; Vista IP law Group, LLP

(57) ABSTRACT

A non-invasive system and method are provided. Brain activity of a user is detected using a non-invasive brain interface when the user is exposed to an external stimulus. The user is determined to be negatively primed by the external stimulus based on the detected brain activity. An alert that the user is being negatively primed by the external stimulus is automatically provided. A tagged training session may be automatically provided to the user in response determining that the user has a negative mental state, thereby promoting a positive mental state of the user. A training session list containing the tagged training session may be automatically modified based on the determined mental state of the user.

30 Claims, 14 Drawing Sheets

(51) Int. Cl.
*A61B 5/245* (2021.01)
*A61B 5/00* (2006.01)
*A61B 5/16* (2006.01)

(52) U.S. Cl.
CPC ............ *A61B 5/245* (2021.01); *A61B 5/6803* (2013.01); *A61B 5/746* (2013.01); *A61B 5/7455* (2013.01); *A61M 21/02* (2013.01); *A61B 2503/12* (2013.01)

(58) Field of Classification Search
CPC ......... A61B 5/165; A61B 5/245; A61B 5/375; A61B 5/4064; A61B 5/486; A61B 5/6803; A61B 5/7455; A61B 5/746; A61M 2021/0027; A61M 2021/0044; A61M 2021/005; A61M 21/00; A61M 21/02; A61M 2205/18; A61M 2205/3306; A61M 2205/3317; A61M 2205/3553; A61M 2205/3592; A61M 2205/52; A61M 2205/581; A61M 2205/582; A61M 2205/583; A61M 2205/8206; A61M 2209/088; A61M 2230/10
See application file for complete search history.

(56) References Cited

U.S. PATENT DOCUMENTS

| | | | |
|---|---|---|---|
| 5,853,370 | A | 12/1998 | Chance et al. |
| 6,231,187 | B1 | 5/2001 | Munoz |
| 6,488,617 | B1 | 12/2002 | Katz |
| 8,209,224 | B2 | 6/2012 | Pradeep |
| 8,473,024 | B2 | 6/2013 | Causevic et al. |
| 8,609,162 | B2 | 12/2013 | Giuliano et al. |
| 8,762,202 | B2 | 6/2014 | Pradeep et al. |
| 9,101,279 | B2 | 8/2015 | Ritchey et al. |
| 9,114,140 | B2 | 8/2015 | Giuliano et al. |
| 9,265,974 | B2 | 2/2016 | You et al. |
| 9,339,227 | B2 | 5/2016 | Darcy et al. |
| 9,417,106 | B2 | 8/2016 | Tobita |
| 9,440,064 | B2 | 9/2016 | Wingeier et al. |
| 9,704,205 | B2 | 7/2017 | Akutagawa et al. |
| 9,712,736 | B2 | 7/2017 | Kearns et al. |
| 9,729,252 | B2 | 8/2017 | Tyler et al. |
| 9,736,603 | B2 | 8/2017 | Osborne et al. |
| 9,943,698 | B2 | 4/2018 | Chase et al. |
| 9,946,344 | B2 | 4/2018 | Ayaz et al. |
| D817,553 | S | 5/2018 | Aaskov et al. |
| D825,112 | S | 8/2018 | Saez |
| 10,091,554 | B1 | 10/2018 | Newell et al. |
| 10,143,414 | B2 | 12/2018 | el Kaliouby et al. |
| 10,188,860 | B2 | 1/2019 | Wingeier et al. |
| 10,234,942 | B2 | 3/2019 | Connor |
| 10,258,760 | B1 | 4/2019 | Sherpa et al. |
| 10,340,408 | B1* | 7/2019 | Katnani .......... H01L 31/022408 |
| 2003/0176806 | A1 | 9/2003 | Pineda et al. |
| 2004/0049134 | A1 | 3/2004 | Tosaya et al. |
| 2005/0273017 | A1 | 12/2005 | Gordon |
| 2006/0150989 | A1 | 7/2006 | Migaly |
| 2006/0161218 | A1 | 7/2006 | Danilov |
| 2008/0177197 | A1 | 7/2008 | Lee et al. |
| 2008/0255949 | A1* | 10/2008 | Genco .................... A61B 5/165 705/14.4 |
| 2009/0083129 | A1 | 3/2009 | Pradeep et al. |
| 2012/0172743 | A1 | 7/2012 | Aguilar et al. |
| 2013/0289385 | A1 | 10/2013 | Lozano et al. |
| 2013/0297599 | A1 | 11/2013 | Henshall |
| 2013/0311132 | A1 | 11/2013 | Tobita |
| 2014/0023999 | A1 | 1/2014 | Greder |
| 2014/0200432 | A1 | 7/2014 | Banerji et al. |
| 2014/0228701 | A1 | 8/2014 | Chizeck et al. |
| 2014/0303450 | A1 | 10/2014 | Caponi |
| 2015/0248651 | A1 | 9/2015 | Akutagawa et al. |
| 2015/0290454 | A1 | 10/2015 | Tyler et al. |
| 2015/0297109 | A1 | 10/2015 | Garten |
| 2015/0338917 | A1 | 11/2015 | Steiner et al. |
| 2015/0351655 | A1* | 12/2015 | Coleman ................ G16H 50/20 600/595 |
| 2015/0355462 | A1 | 12/2015 | Saito et al. |
| 2016/0077547 | A1* | 3/2016 | Aimone ................ A61B 5/1114 345/8 |
| 2016/0220163 | A1 | 8/2016 | Yamada |
| 2016/0242690 | A1 | 8/2016 | Principe et al. |
| 2016/0270656 | A1 | 9/2016 | Samec et al. |
| 2017/0042439 | A1 | 2/2017 | Yeow |
| 2017/0188876 | A1 | 7/2017 | Marci et al. |
| 2017/0202518 | A1 | 7/2017 | Furman et al. |
| 2017/0229037 | A1 | 8/2017 | Gazzaley |
| 2017/0262943 | A1 | 9/2017 | Akutagawa et al. |
| 2017/0347906 | A1* | 12/2017 | Intrator ................ A61B 5/7264 |
| 2017/0352283 | A1 | 12/2017 | Lau |
| 2018/0092557 | A1 | 4/2018 | Bickford et al. |
| 2018/0278984 | A1 | 9/2018 | Aimone |
| 2019/0021657 | A1 | 1/2019 | Mohammadrezazadeh et al. |
| 2019/0082990 | A1 | 3/2019 | Poltorak |
| 2019/0200888 | A1 | 7/2019 | Poltorak |
| 2019/0201691 | A1 | 7/2019 | Poltorak |
| 2019/0224441 | A1 | 7/2019 | Poltorak |
| 2019/0246929 | A1 | 8/2019 | Poltorak |
| 2019/0247662 | A1 | 8/2019 | Poltorak |
| 2019/0321583 | A1 | 10/2019 | Poltorak |
| 2020/0281495 | A1* | 9/2020 | Eroglu ................. A61B 5/4088 |

FOREIGN PATENT DOCUMENTS

| | | |
|---|---|---|
| WO | WO2014055932 | 4/2014 |
| WO | 2939706 | 11/2015 |
| WO | WO2016022414 | 2/2016 |
| WO | WO2019104008 | 5/2019 |

OTHER PUBLICATIONS

PCT International Search Report and Written Opinion for International Appln. No. PCT/US2019/024027, Applicant HI LLC, forms PCT/ISA/210, 220 and 237 dated Aug. 19, 2019 (13 pages).

Lee, B.T., Seok, J.H., Lee., B.C, Cho, S.W., Chai, J.H., Choi, I.G., Ham, B.J., "Neural correlates of affective processing in response to sad and angry facial stimuli in patients with major depressive disorder," Prog Neuropsychopharmacol Biol Psychiatry, 32(3), 778-85 (2008.

A.C. Felix-Ortiz, A.C., Burgos-Robles, A., Bhagat, N.D., Leppla, C.A., Tye, K.M., "Bidirectional modulation of anxiety-related and social behaviors by amygdala projections to the medial prefrontal cortex," Neuroscience 321, 197-209 (2016).

Beauregard, M., Levesque, J. & Bourgouin, P., "Neural correlates of conscious self-regulation of emotion," J. Neurosci. (2001): 21, RC165.

Phan, K. L., Wager, T., Taylor, S. F. & Liberzon, I., "Functional neuroanatomy of emotion: a meta-analysis of emotion activation studies in PET and fMRI," Neuroimage, 16, 331-348 (2002).

Canli, T. & Amin, Z., "Neuroimaging of emotion and personality: scientific evidence and ethical considerations," Brain Cogn., 50, 414-431 (2002).

McCloskey, M. S., Phan, K. L. & Coccaro, E. F., "Neuroimaging and personality disorders," Curr. Psychiatry Rep., 7, 65-72 (2005).

Heekeren, H. R., Marrett, S., Bandettini, P. A. & Ungerleider, L. G., "A general mechanism for perceptual decision-making in the human brain," Nature, 431, 859-862 (2004).

Shin LM, Rauch SL, Pitman RK., "Amygdala, Medial Prefrontal Cortex, and Hippocampal Function in PTSD," Ann N Y Acad Sci., 1071(1) (2006).

Lis E, Greenfield B, Henry M, Guile JM, Dougherty G., "Neuroimaging and genetics of borderline personality disorder: a review," J Psychiatry Neurosci., 32(3), 162-173 (2007).

Etkin A, Wager TD, "Functional neuroimaging of anxiety: a meta-analysis of emotional processing in PTSD, social anxiety disorder, and specific phobia," Am J Psychiatry, 164(10), 1476-1488 (2007).

Hamilton, P., Etkin A., "Functional Neuroimaging of Major Depressive Disorder: A Meta-Analysis and New Integration of Baseline Activation and Neural Response Data", Am J Psychiatry, 169(7), 693-703 (2012).

(56) References Cited

OTHER PUBLICATIONS

Sheline YI, Price JL, Yan Z, Mintun MA, "Resting-state functional MRI in depression unmasks increased connectivity between networks via the dorsal nexus," Proc Natl Acad Sci., 107(24), 11020-11025 (2010).
Bari A, Robbins TW, "Inhibition and impulsivity: Behavioral and neural basis of response control," Prog Neurobiol., 108:44-79 (2013).
Kagias, Konstantinos et al. "Neuronal responses to physiological stress," Frontiers in genetics, 3:222 (2012).
Clark, Ian A., et al., "First steps in using machine learning on fMRI data to predict intrusive memories of traumatic film footage", 0005-7967/ 2014 the Authors. Published by Elsevier Ltd. Behaviour Research and Therapy. This is an open access article under the CC by license (http://creativecommons.org/licenses/by/3.0/); 10 pgs.
George, Mark S., M.D., "Changes in Mood and Hormone Levels After Rapid-Rate Transcranial Magnetic Stimulation (rTMS) of the Prefrontal Cortex", Journal of Neuropsychiatry, vol. 8, No. 2, Spring 1996, 9 pages.
Milad, M. R., et al., "Neuroscience of fear extinction: Implications for assessment and treatment of fear-based and anxiety related disorders", Behaviour Research and Therapy (2014), http://dx.doi.org/10.1016/j.brat.2014.08.006, 7 pages.
S.Z.K, Tan et al.,"Eternal sunshine of the neuromodulated mind: Altering fear memories through neuromodulation", Experimental Neurology 314 (2019) 9-19, 11 pages.
Zhang, Fei-Fei, et al., "Brain structure alterations in depression: Psychoradiological evidence", CNS Neurosci T 2018, John Wiley & Sons Ltd her. 2018;24:994-1003, 10 pages.
Non-Final Office Action dated Oct. 4, 2019, 26 pages.
Amendment and response filed Nov. 8, 2019, 11 pages.
Final Office Action dated Jan. 27, 2020, 21 pages.
Amendment and response filed Feb. 26, 2020, 14 pages.
Non-Final Office Action dated Mar. 23, 2020, 15 pages.
PCT International Search Report and Written Opinion for International Appln. No. PCT/US2019/043768, Applicant HI LLC, forms PCT/ISA/210, 220 and 237 dated Oct. 15, 2019 (11 pages).
Marianna Papadopoulou et al.; "Event-related potentials before saccades and antisaccades and their relation to reaction time", Experimental Brain Research, Springer, Berlin, DE, vol. 205, No. 4, Aug. 14, 2010, pp. 521-531, XP019840052.
Frank Schmal et al., "Effect of Ethanol on Visual-Vestibular Interactions During Vertical Linear Body Acceleration", Alcoholism: Clinical and Experimental Research, vol. 27, No. 9, Sep. 1, 2003, pp. 1520-1526, XP055626675.
Judith Amores, et al., "Promoting Relaxation Using Virtual Reality, Olfactory Interfaces and Wearable EEG," 2018 IEEE 15th International Conference on Waerable and Implantable Body Sensor Networks; Mar. 4, 2018, (4 pages).
PCT International Search Report and Written Opinion for International Appln. No. PCT/US2020/029031, Applicant HI LLC, forms PCT/ISA/210, 220 and 237 dated Sep. 2, 2020 (18 pages).
Final Office Action dated Jul. 29, 2020, 27 pages.
PCT International Search Report and Written Opinion for International Appln. No. PCT/US2020/025971, Applicant HI LLC, forms PCT/ISA/210, 220 and 237 dated Sep. 15, 2020 (15 pages).
Stefan K. Ehrlich, et al., "A closed-loop, music-based brain-computer interface for emotion mediation," PLoS ONE 14(3): e0213516. https://doi.org/10.1371/journal.pone.0213516; Mar. 18, 2019.
Patrick Gomez, et al., "Relationships Between Musical Structure and Psychophysiological Measures of Emotion", American Psychological Association, vol. 7, No. 2, 2007, pp. 377-387, 10 pages.
Fernando Lopes da Silva, "EEG and MEG: Relevance to Neuroscience", Center of Neuroscience; http://dx.doi.org/10.1016/j.neuron.2013.10.017; 17 pages.
Elena Boto, et al., "A new generation of magnetoencephalography: Room temperature measurements using optically-pumped magnetometers", NeuroImage 149 (2017) 404-414; 11 pages.
Stanislas Dehaene, et al., "Imaging unconscious semantic priming", Nature; vol. 395; Oct. 8, 1998; 4 pages.
John D. E. Gabrieli, et al., "The role of left prefrontal cortex in language and memory", Proc. Natl. Acad. Sci. USA, vol. 95, pp. 906-913, Feb. 1998; 8 pages.
Yang Jiang, et al., "Turning up the Old Brain with New Tricks: Attention Training via Neurofeedback", Frontiers in Aging Neuroscience; Mar. 2017; vol. 9; Article 52; 9 pages.
Peter Lintelle, Sensory Marketing Aspects: Priming, Expectations, Crossmodal Correspondences & More; CreateSpace Independent Publishing Platform, Jul. 23, 2014, ISBN-10: 1500616400, ISBN-13: 978-1500616403; 3 pages.
Samat Moldakarimova, et al., "Perceptual priming leads to reduction of gamma frequency oscillations", PNAS, Mar. 23, 2010, vol. 107, No. 12; 6 pages.
M. Teplan, "Fundamentals of EEG Measurement", Measurement Science Review, vol. 2, Section 2, 2002; 11 pages.

\* cited by examiner

FIG. 2A — PRESENTLY PRESENTED TRAINING SESSION → TRAINING SESSION 1; TRAINING SESSION 2; TRAINING SESSION 3; TRAINING SESSION 4; TRAINING SESSION 5

FIG. 2B — RETAINED TRAINING SESSION → TRAINING SESSION 1; TRAINING SESSION 2; TRAINING SESSION 3; TRAINING SESSION 4; TRAINING SESSION 5

FIG. 2C — DELETED TRAINING SESSION → TRAINING SESSION 1 (struck through); TRAINING SESSION 2; TRAINING SESSION 3; TRAINING SESSION 4; TRAINING SESSION 5

FIG. 2D — PRESENTLY PRESENTED TRAINING SESSION → TRAINING SESSION 1; TRAINING SESSION 2; TRAINING SESSION 3; TRAINING SESSION 4; TRAINING SESSION 5; ADDED TRAINING SESSIONS → TRAINING SESSION 6; TRAINING SESSION 7; TRAINING SESSION 8

FIG. 2E — DELETED TRAINING SESSION → TRAINING SESSION 1 (struck through); DELETED TRAINING SESSION → TRAINING SESSION 2 (struck through); TRAINING SESSION 3; DELETED TRAINING SESSION → TRAINING SESSION 4 (struck through); TRAINING SESSION 5

NON-INVASIVE SYSTEMS AND METHODS FOR THE DETECTION AND MODULATION OF A USER'S MENTAL STATE THROUGH AWARENESS OF PRIMING EFFECTS

RELATED APPLICATION DATA

Pursuant to 35 U.S.C. § 119(e), this application claims the benefit of U.S. Provisional Application Ser. No. 62/859,880, filed Jun. 11, 2019, and U.S. Provisional Application Ser. No. 62/891,128, filed Aug. 23, 2019, which are expressly incorporated herein by reference.

FIELD OF THE INVENTION

The present inventions relate to methods and systems for non-invasive measurements in the human body, and in particular, methods and systems related to detecting a mental state of a human and providing neurofeedback of that mental state through awareness of priming effects.

BACKGROUND OF THE INVENTION

It is generally known that awareness of one's subconscious mental state, such as anxiety, focus, attention, creativity, positive or negative reflections/attitude on experiences or the use of objects, the employment of certain critical cognitive brain areas, etc., may lead to better emotional mood regulation and more objective decision-making. However, the conscious mind typically has peripheral or no awareness of subconscious mental states. Thus, if a person has a negative or unhealthy mental state (e.g., anxiety) within the context of a life or work experience, such person may not be aware of such mental state, and therefore, will be unable to take corrective actions (e.g., modifying or creating a new life or work experience) in order to alleviate or change this mental state.

As one particular example, in everyday life, one is often subjected to priming effects, whereby exposing a person to one stimulus to influence a response from that person to a subsequent stimulus, without conscious guidance or intention (see en.wikipedia.org/wiki/Priming_(psychology); blog.motivemetrics.com/What-is-Priming-A-Psychological-Look-at-Priming-Consumer-Behavior). Priming operates on the nonconscious form of human memory concerned with perceptual identification of words and objects, and activates particular representations or associations in memory just before carrying out an action or task. For example, a person who sees the word "yellow" will be slightly faster to recognize the word "banana," since concepts of "yellow" and "banana" are closely associated in memory. Priming can be used to train a person's memory in both positive and negative ways (see www.psychologytoday.com/us.basics/priming).

The priming effect is the basis for advertisements, political communications, religious messages, or other types of social, environmental, and training communications intended to influence, manipulate, or exploit the consumer's/listener's behavior (e.g., by targeting fear, social status comparison, inferior status, or targeting other types of emotions or comparisons), which the consumer/listener is typically unaware of. In this regard, priming can be considered to have a negative effect on the person that is subjected to the priming effect. Indeed, many sales and marketing personnel are trained to employ various priming techniques on consumers/listeners (see Lintelle, P, "*Sensory Marketing Aspects: Priming, Expectations, Crossmodal Correspondence& More*," Book Review, The Journal for Decision Makers).

Thus, there is a social norm in society that anyone engaged in priming can say whatever they want without consequences, i.e., by priming anything. The lack of awareness of how society is being tricked, manipulated, influenced, exploited, or preyed on, through priming typically on a daily basis may have dramatic effects on an individual's daily behavior, actions, and decisions, since such individual will not be aware of such negative tactics.

Neurofeedback, which is a form of biofeedback that uses real-time modulation of brain activity to enhance brain function and behavioral performance, has been proposed (see Enriquez-Geppert, Stefanie, et al., "EEG-Neurofeedback as a Tool to Modulate Cognition and Behavior: A Review Tutorial," *Frontiers in Human Neuroscience* (February 2017); Orndorff-Plunkett, F, et al., "Assessing the Effectiveness of Neurofeedback Training in the Context of Clinical and Social Neuroscience," *Brain Sci.,* 7, 95 (2017); and Marzbani, H, "Neurofeedback: A Comprehensive Review on System Design, Mythology and Clinical Applications," *Basic and Clinical Neuroscience,"* 7(2), 143-158 (2016)), as:

(1) a therapeutic tool to normalize patients' deviating brain activity in order to influence symptoms (e.g., to improve attention in people suffering from neural disease or affliction, such as Alzheimer's disease or vascular dementia in the elderly, Parkinson's, and attention deficit hyperactivity disorder (ADHD) in children (see Jiang, Y, et al., "Tuning Up the Old Brain with New Tricks: Attention Training via Neurofeedback," *Frontiers in Aging Neuroscience,* 13 Mar. 2017; Bussalb, A, et al., "Clinical and Experimental Factors Influencing the Efficacy of Neurofeedback in ADHD: A Meta-Analysis," *Frontiers in Psychiatry*, Volume 10, Article 35 (February 2019), post-stroke recovery (see Pfurtscheller, G., et al., "Future Prospects of ERD/ERS in the Context of Brain-Computer Interface (BCI) Developments," *Prog. Brain Res.* 159, 433-437 (2016), cocaine use disorder (CUD) (see Kirschner, M, et al., "Self-Regulation of the Dopaminergic Reward Circuit in Cocaine Users with Mental Imagery and Neurofeedback," *EBioMedicine* 37 (2018) 489-498), and various other ailments), depression (Fitzgerald, P, et al., "Gamma Oscillations as a Biomarker for Major Depression: an Emerging Topic," *Translational Psychiatry* (2018) 8:177), eating disorders (Imperatori, C, et al., "Feedback-Based Treatments for Eating Disorders and Related Symptoms: A Systematic Review of the Literature," *Nutrients,* 10, 1806 (2018));

(2) a so-called peak-performance training to enhance cognitive performance and emotional regulation in healthy participants (see Gruzelier, "EEG-Neurofeedback for Optimizing Performance. III: A Review of Methodological and Theoretical Considerations," *Neurosci. Biobehav. Rev.* 44, 159-182 (2014); Dekker, M. K., et al., "The Time-Course of Alpha Neurofeedback Training Effects in Healthy Participants," *Biol. Psychol.* 95, 70-73 (2014); Wang, J. R., et al., Neurofeedback Training Improves Attention and Working Memory Performance," *Clin. Neurophysiol*, 124, 2406-2420 (2013); Johnston, S. J., et al., "Neurofeedback: A Promising Tool for the Self-Regulation of Emotion Networks," *Neuroimage,* 49, 1066-1072 (2010); Lorenzetti, V, et al., "Emotion Regulation Using Virtual Environments and Real-Time fMRI Neurofeedback," *Frontiers in Neurology*, Vol. 9, 390 (2018)); and (3) an experimental method to investigate the causal role of specific neural events (such as brain oscillations) for cognition and behavior (Jensen, O., et al., "Using Brain-Computer Interfaces and Brain-State Dependent Stimulation as Tools in Cognitive Neuroscience," *Front. Psychol.* (2011); van Schie, H. T., et al., "Neurofeedback as an Experimental Technique: Controlled Theta Oscillations Modulate Reaction times in a Sternberg Working Memory Task," *Conference Program and Abstracts* (2014); Guhathakurta, D., et al., "Computational Pipeline for NRIS-EEG Joint Imaging of tDCS-Evoked Cerebral Responses—An Application in Ischemic Stroke," *Front. Neurosci,* 10:261 (2016); Royter, V., et al., "Brain State-Dependent Closed-Loop Modulation of Paired Associative Stimulation Controlled by Sensorimotor Desynchronization," Front. Cell. Neurosci. (2016).

Prior existing technology, as applied to neurofeedback sessions, includes general state awareness through the measurement of electrical brain activity, e.g., electroencephalography (EEG) (see, e.g., Jiang, Y, et al., "Tuning Up the Old Brain with New Tricks: Attention Training via Neurofeedback," *Frontiers in Aging Neuroscience*, 13 March 2017); or functional magnetic resonance imaging (fMRI) (see, e.g., Lorenzetti, V, et al., "Emotion Regulation Using Virtual Environments and Real-Time fMRI Neurofeedback," *Frontiers in Neurology*, Vol. 9, 390 (2018)).

However, EEG and fMRI are limited in their form factor and have limitations on spatial resolution, and thus, cannot effectively provide the necessary neural feedback sessions to users in a normal life and work environment. In particular, fMRI requires large magnets enclosed within a tunnel tube-type enclosure that patients lie within (similar to magnetic resonance imaging (MRI) machines) which are known to cause claustrophobia, and thus, cannot be scaled to wearable or portable form factors. In order to obtain a signal, EEG electrodes require the use of a "conductive gel," since the electrodes need to be "wet" in order to bridge the gap between skin and the EEG electrodes. Also, in order to have an effective EEG recording, the EEG electrodes are required to be in direct contact with the user's skull. The EEG signal is known to be distorted due to noise from the skull and other brain tissue. Also, users typically experience pressure and discomfort when wearing an EEG device and removal of the gel from user's hair often requires a special washing solution since the gel is known to have an adhesive effect on the hair and skull.

Furthermore, currently proposed neurofeedback techniques have not addressed priming effects caused by third parties, such as advertisers or salespersons, that do not have the best interests of the user in mind. In fact, because EEG and fMRI cannot effectively be used in a normal life and work environment due to the reasons discussed above, these technologies are unsuitable for addressing such priming effects, which predominantly occur in a normal life environment (e.g., when the user is (a) walking around a store, shopping malls, airport terminals, amusement parks, hotel common areas and lobbies, eating establishments; (b) commuting, e.g., to/from work or to/from school, and being exposed to street billboards, advertisements on public terminals, benches, and transportation vehicles (buses, trains, taxis, etc.); (c) watching or listening to television and radio programs; (d) surfing the world-wide-web).

There, thus, remain a need to make a person consciously aware of when a third party is priming the person, and to adjust any negative mental state of the person as a result of such priming, so that such person may better regulate his or her emotions or make more objective decisions.

SUMMARY OF THE INVENTION

In accordance with a first aspect of the present inventions, a non-invasive anti-priming system comprises a non-invasive brain interface assembly configured for detecting brain activity of a user when the user is exposed to an external stimulus (e.g., one of an advertisement, social or political message, and a sales tactic). In one embodiment, the non-invasive brain interface assembly is an optical measurement assembly. In another embodiment, the non-invasive brain interface assembly is a magnetic measurement assembly. The non-invasive brain interface assembly may comprise, e.g., at least one detector configured for detecting energy from a brain of the user, and processing circuitry configured for identifying the brain activity in response to detecting the energy from the brain of the user. The non-invasive brain interface assembly may comprise a head-worn unit carrying the at least one energy source, and an auxiliary non-head-worn unit carrying the processing circuitry.

The non-invasive anti-priming system further comprises at least one processor configured for determining that the user is being negatively primed by the external stimulus based on the detected brain activity. In one embodiment, the processor(s) is configured for determining that the user is being negatively primed by the external stimulus by determining that the user has a negative mental state (e.g., one of anxiety and fear) based on the detected brain activity. The processor(s) may be configured for being programmed with the negative mental state.

The non-invasive anti-priming system further comprises a biofeedback assembly configured for automatically providing an alert that the user is being negatively primed by the external stimulus. In one embodiment, the biofeedback assembly is configured for providing/directing vibrational signals to the user indicative of the determined mental state of the user through peripheral somatosensation. The vibrational signals may be encoded with one or more messages. In another embodiment, the biofeedback assembly is configured for providing/directing audio or visual alert signals to the user.

In an optional embodiment, the biofeedback assembly is further configured for automatically providing neural feedback to the user that promotes a positive mental state (e.g., one of joy, relaxation, and a cognitive state) of the user in response to the processor determining that the user is being negatively primed by the external stimulus. The processor(s) may be configured for being programmed with the positive mental state. The neural feedback may comprise a training session, e.g., instructional media promoting a positive mental state of the user and/or a mental exercise administered to the user to promote a positive mental state of the user. In one embodiment, the biofeedback assembly comprises a non-wearable peripheral feedback device configured for automatically providing the neural feedback to the user, and a wearable feedback device configured for automatically providing the alert to the user.

In accordance with a second aspect of the present inventions, a method of correcting negative priming of a user comprises detecting brain activity of a user using a non-invasive brain interface when the user is exposed to an external stimulus (e.g., one of an advertisement, social or political message, and a sales tactic). In one method, the brain activity is optically detected. In another method, the brain activity is magnetically detected. The brain activity of the user may be detected, e.g., by detecting energy from a brain of the user, and identifying the brain activity in response to detecting the energy from the brain of the user.

The method further comprises determining that the user is being negatively primed by the external stimulus based on the detected brain activity. In one method, determining that the user is being negatively primed by the external stimulus comprises determining that the user has a negative mental state (e.g., one of anxiety and fear) based on the detected brain activity.

The method further comprises automatically providing an alert that the user is being negatively primed by the external stimulus. In one method, automatically providing the alert that the user comprises providing/directing vibrational signals to the user indicative of the determined mental state of the user through peripheral somatosensation. The vibrational signals may be encoded with one or more messages. In another method, automatically providing the alert that the user comprises providing/directing audio or visual alert signals to the user.

An optional method further comprises automatically providing neural feedback to the user that promotes a positive mental state (e.g., one of joy, relaxation, and a cognitive state) of the user in response to the processor determining that the user is being negatively primed by the external stimulus. The neural feedback may comprise a training session, e.g., instructional media promoting a positive mental state of the user and/or a mental exercise administered to the user to promote a positive mental state of the user.

In accordance with a third aspect of the present inventions, a non-invasive system comprises a non-invasive brain interface assembly configured for detecting brain activity of a user. In one embodiment, the non-invasive brain interface assembly is an optical measurement assembly. In another embodiment, the non-invasive brain interface assembly is a magnetic measurement assembly. The non-invasive brain interface assembly may comprise, e.g., at least one detector configured for detecting energy from a brain of the user, and processing circuitry configured for identifying the brain activity in response to detecting the energy from the brain of the user. The non-invasive brain interface assembly may comprise a head-worn unit carrying the at least one energy source, and an auxiliary non-head-worn unit carrying the processing circuitry.

The non-invasive system further comprises at least one processor configured for determining a negative mental state (e.g., one of anxiety and fear) of a user based on the detected brain activity. In an optional embodiment, the processor(s) is further configured for determining that the user is being negatively primed by the external stimulus (e.g., one of an advertisement, social or political message, and a sales tactic) based on the determined negative mental state of the user. The processor(s) may be configured for being programmed with the negative mental state.

The non-invasive system further comprises a biofeedback assembly configured for automatically providing a training session (e.g., instructional media promoting a positive mental state of the user and/or a mental exercise administered to the user to promote a positive mental state of the user) to the user in response to the determined negative mental state of the user, thereby promoting a positive mental state (e.g., one of joy, relaxation, and a cognitive state) of the user. The processor(s) may be configured for being programmed with the positive mental state. In an optional embodiment, the processor(s) is further configured for selecting one of a plurality of training session lists corresponding to the positive mental state, and automatically providing a tagged training session from the selected training session list to the user in response to the determined negative mental state of the user.

In accordance with a fourth aspect of the present inventions, a method of promoting a positive mental state of a user comprises detecting brain activity of a user using a non-invasive brain interface. In one method, the brain activity is optically detected. In another method, the brain activity is magnetically detected. The brain activity of the user may be detected, e.g., by detecting energy from a brain of the user, and identifying the brain activity in response to detecting the energy from the brain of the user.

The method further comprises determining that the user has a negative mental state (e.g., one of anxiety and fear) based on the detected brain activity. An optional method further comprises determining that the user is being negatively primed by an external stimulus (e.g., one of an advertisement, social or political message, and a sales tactic) based on the determined negative mental state of the user.

The method further comprises automatically providing a tagged training session (e.g., instructional media promoting a positive mental state of the user and/or a mental exercise administered to the user to promote a positive mental state of the user) to the user in response to the determined negative mental state of the user, thereby promoting the positive mental state (e.g., one of joy, relaxation, and a cognitive state) of the user. An optional method further comprises selecting one of a plurality of training session lists corresponding to the programmed positive mental state. In this case, the tagged training session is automatically provided from the selected training session list to the user in response to the determined negative mental state of the user.

In accordance with a fifth aspect of the present inventions, a non-invasive system comprises a biofeedback assembly configured for providing a list of training sessions to a user, and a non-invasive brain interface assembly configured for detecting brain activity of the user while the biofeedback assembly provides a tagged training session (e.g., instructional media promoting a positive mental state of the user and/or a mental exercise administered to the user to promote a positive mental state of the user) in the training session list to the user. In one embodiment, the non-invasive brain interface assembly is an optical measurement assembly. In another embodiment, the non-invasive brain interface assembly is a magnetic measurement assembly. The non-invasive brain interface assembly may comprise, e.g., at least one detector configured for detecting energy from a brain of the user, and processing circuitry configured for identifying the brain activity in response to detecting the energy from the brain of the user. The non-invasive brain interface assembly may comprise a head-worn unit carrying the at least one energy source, and an auxiliary non-head-worn unit carrying the processing circuitry.

The non-invasive system further comprises at least one processor configured for determining a mental state of the user based on the detected brain activity, and automatically modifying the training session list based on the determined mental state of the user. In one embodiment, the training session list corresponds to a desired mental state, e.g., a positive mental state, such as joy, relaxation, and a cognitive state. In this case, if the determined mental state matches the desired mental state, the processor(s) may be configured for automatically modifying the training session list to retain the tagged training session in the training session list and/or to include more training sessions in the training session list having the same attributes as the tagged training session, and if the determined mental state does not match the desired mental state, the processor(s) may be configured for automatically modifying the training session list to discard the tagged training session from the training session list and/or to include less training sessions in the training session list having the same attributes as the tagged training session.

In accordance with a sixth aspect of the present inventions, a method of customizing a list of training sessions comprises providing a tagged training session (e.g., instructional media promoting a positive mental state of the user and/or a mental exercise administered to the user to promote a positive mental state of the user) in a list of training sessions to the user. The method further comprises detecting brain activity of a user using a non-invasive brain interface while the tagged training session is concurrently being provided to the user. In one method, the brain activity is optically detected. In another method, the brain activity is magnetically detected. The brain activity of the user may be detected, e.g., by detecting energy from a brain of the user, and identifying the brain activity in response to detecting the energy from the brain of the user.

The method further comprises determining a mental state of the user based on the detected brain activity, and automatically modifying the training session list based on the determined mental state of the user. In one method, the training session list corresponds to a desired mental state, e.g., a positive mental state, such as joy, relaxation, and a cognitive state. In this case, if the determined mental state matches the desired mental state, the processor(s) may be configured for automatically modifying the training session list to retain the tagged training session in the training session list and/or to include more training sessions in the training session list having the same attributes as the tagged training session, and if the determined mental state does not match the desired mental state, the processor(s) may be configured for automatically modifying the training session list to discard the tagged training session from the training session list and/or to include less training sessions in the training session list having the same attributes as the tagged training session.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIGS. 2A-2E are training sessions lists that are modified by the non-invasive anti-priming system of FIGS. 1A and 1B;

DETAILED DESCRIPTION OF THE EMBODIMENTS

Figure 1A:
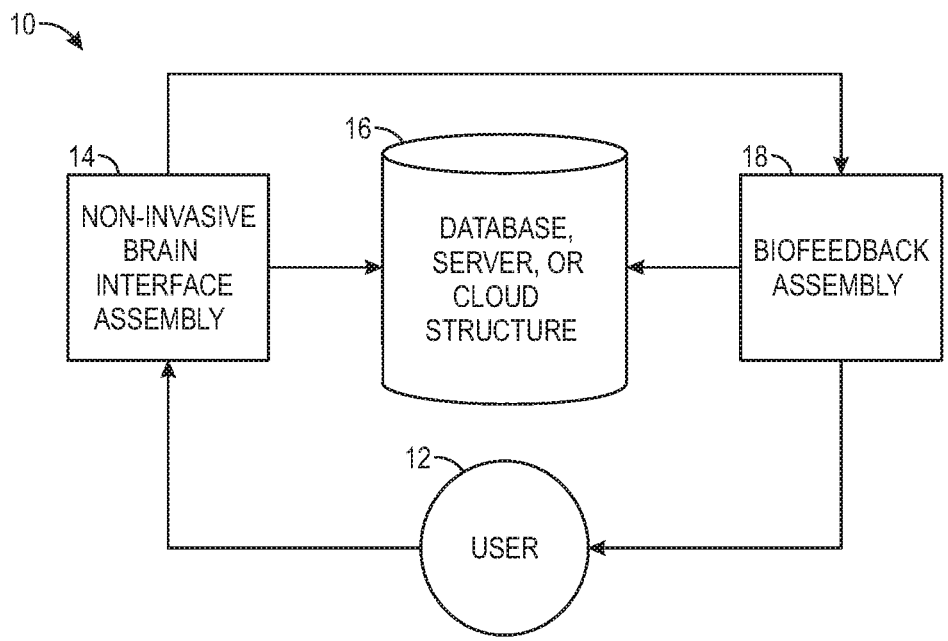
FIG. 1A is a block diagram of a non-invasive anti-priming system constructed in accordance with one embodiment of the present inventions.

The non-invasive anti-priming systems described herein use higher fidelity processes to acquire neural signals from an individual, compared to EEG systems, and do not require heavy or bulky magnet tunnel tube-type enclosures like fMRI systems require, and thus, may be implemented in a small, portable, and wearable form factor for use by an individual in a normal life and work environment.

For purposes of this specification, a "normal life and work environment" is an environment that is usual and ordinary, and thus, necessitates that the user be able to freely ambulate without any physical hindrance by the non-invasive anti-priming system or other system to which the non-invasive anti-priming system is coupled or otherwise is an adjunct. Thus, a normal life and work environment excludes settings in which the user is unable to freely move (e.g., any clinical setting in which a conventional magnetic resonance imaging (MRI) machine or computed tomography (CT) could potentially be used to detect neural activity from the user and hinder the user's movement). In alternative embodiments, the non-invasive anti-priming systems described herein may be non-portable and/or non-wearable in cases where it is suitable for the non-invasive anti-priming system to be operated outside of a normal life and working environment.

The higher quality neural data acquired by the non-invasive anti-priming systems described herein lead to granular insights on how individual areas in the brain of the individual are responding together, and create new insights on cause and effect on priming effects on the brain of the individual, in effect decoding what third parties, such as advertisers or salespersons, are attempting to accomplish, thereby unveiling their priming strategies and tactics.

Thus, the non-invasive anti-priming systems described herein may determine when an individual (e.g., working professional, athlete, student, consumers, anyone with a mental disorder/dysfunction) is being primed (e.g., tricked, influenced, manipulated, exploited, preyed on, etc.) and make the individual aware that he or she is being primed, so that the individual will be better informed in order to exercise better judgment in the face of a particular priming stimulus (e.g., advertisement, social or political message, or sales tactic) prior to or concurrent with the triggering of negative emotions of the individual that may otherwise cause the individual to make an unwise decision based on undesired external pressures. Knowing that the priming effects may be detected by the non-invasive anti-priming systems, the individual may even learn to embrace such priming effects, and use such priming as an advantage by making the individual hyper-aware of his or her mental state. Each priming stimulus can be tagged by the individual's brain signal, labeling it by the priming tactic and providing user awareness.

In addition to, or as an alternative to, making the individual aware that he or she is being primed, the non-invasive anti-priming systems described herein may also provide training sessions to the individual after detection of the priming effect on the individual. Each training session may be customized to the mental state of the individual, i.e., customized in such a manner than when neurofeedback is provided to the individual via the training session, the manner in which the brain resonates is changed. That is, the individual may be placed into a more positive mental state, thereby counteracting the negative mental state (e.g., fear or anxiety) in which the priming effect may have otherwise placed the individual. The individual may have the ability and choice to select which positive mental state the individual is to be placed by selecting one of a variety of different customized training sessions.

As such, the non-invasive anti-priming systems described herein level the playing field, so that society is no longer being negatively primed (e.g., tricked, manipulated, influenced, exploited, or preyed on) at will.

Figure 1B:
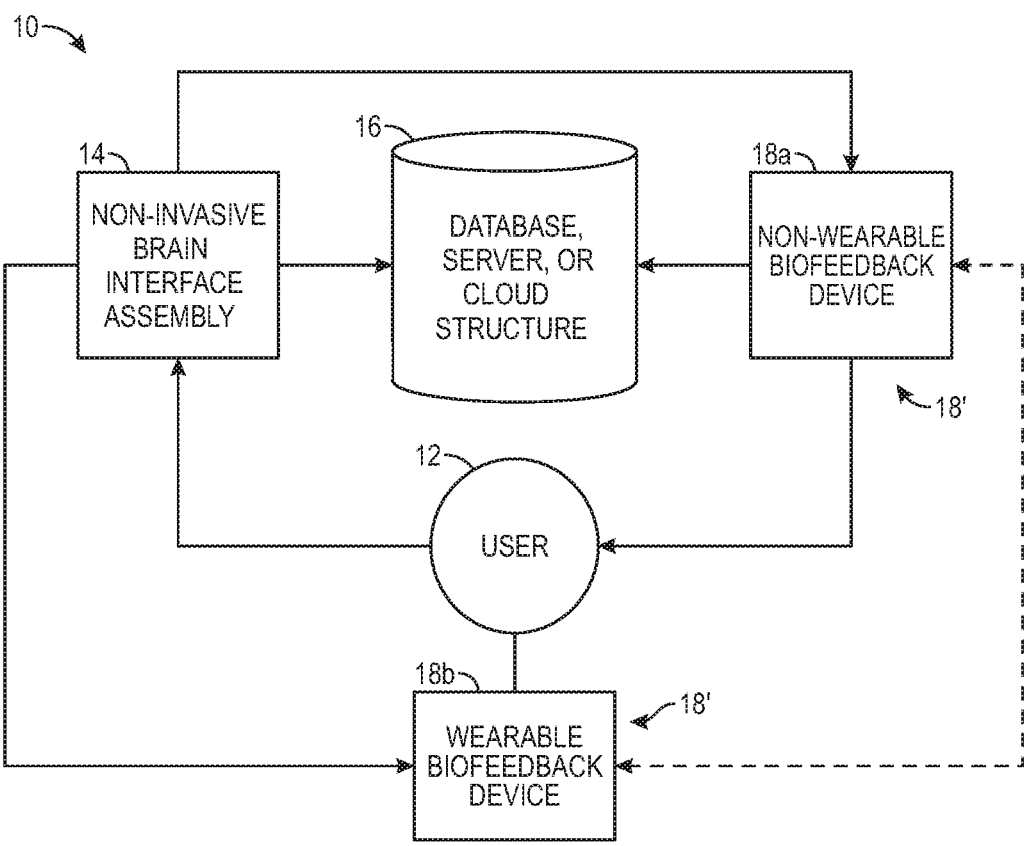
FIG. 1B is a block diagram of a non-invasive anti-priming system constructed in accordance with another embodiment of the present inventions.

Referring now to FIGS. 1A and 1B, a generalized embodiment of a non-invasive anti-priming system 10 constructed in accordance with the present inventions will be described. The non-invasive anti-priming system 10 comprises a non-invasive brain interface assembly 14 configured for detecting brain activity of a user 12. As will be discussed in further detail below, the brain interface assembly 14 can be optically-based, magnetically-based, or based on any other modality that enables it to non-invasively detect brain activity of the user 12 through the intact skin and skull of the user 12, as will be described below, and is designed to be worn by the user 12. As will also be discussed in further detail below, the non-invasive brain interface assembly 14 is portable in that it can be worn by the user 12. The brain interface assembly 14 is configured for determining whether the user 12 is being primed by an external stimulus (e.g., advertisement, social or political message, or sales tactic), although this function can be performed by other processing components in the non-invasive anti-priming system 10, as described in further detail below. The external stimulus that primes the user 12 may originate from an external source, e.g., a radio or television, although in alternative embodiments, the external stimulus may actually originate from peripheral components of the anti-priming system 10, itself, as discussed in detail below.

Priming of the user 12 may be determined by detecting a negative mental state (e.g., fear or anxiety) based on the detected brain activity in any one of a variety of manners. For example, the brain interface assembly 14 may measure the ratio of certain frequency bands associated with anxiety versus relaxation. In one embodiment, a univariate approach in detecting the mental state of the user 12 is being primed may be performed, i.e., the brain activity can be detected in a plurality (e.g., thousands) of separable cortical modules of the user 12, and the brain activity obtained from each cortical module can be analyzed separately and independently. In another embodiment, a multivariate approach in detecting the mental state of the user 12 may be performed, i.e., the brain activity can be detected in a plurality (e.g., thousands) of separable cortical modules of the user 12, and the full spatial pattern of the brain activity obtained from the cortical modules can be assessed together.

Any one of a variety of data models can be used to classify the mental state of the user 12, and will highly depend on the characteristics of brain activity that are input onto the data models. Such characteristics of brain activity may typically be extracted from the spatiotemporal brain activity that is captured, and can include, e.g., location of signal, fine grained pattern within or across locations, amplitude of signal, timing of response to behavior, magnitude of frequency bands of the signal (taking the Fourier transform of the time series), ratio of magnitude of frequency bands, cross-correlation between time series of signal between two or more locations captured simultaneously, spectral coherence between two or more locations captured simultaneously, components that maximize variance, components that maximize non-gaussian similarity, etc. The characteristics of brain activity selected to be input into the data models must be considered in reference to univariate and multivariate approaches, since the univariate approach, e.g., focuses on a single location, and therefore will not take advantage of features that correlate multiple locations. The characteristics of the brain activity can be extracted from preprocessed raw data recorded during situations of patterns of thought and perception in everyday life, which are characterized by a continually changing stream of consciousness. The preprocessing of the raw data typically involves filtering the data (either in the time domain or the frequency domain) to smooth, remove noise, and separate different components of signal.

Selecting a data model will be heavily dependent on whether the data is labeled or unlabeled (meaning is it known what the user is doing at the time that the brain activity is detected), as well as many other factors (e.g., is the data assumed to be normally distributed, is the data assumed relationship linear, is the data assumed relationship non-linear, etc.) Models can include, e.g., support vector machines, expectation maximization techniques, naïve-Bayesian techniques, neural networks, simple statistics (e.g., correlations), deep learning models, pattern classifiers, etc.

These data models are typically initialized with some training data (meaning that a calibration routine can be performed on the user to determine what the user is doing). If no training information can be acquired, such models can be heuristically initialized based on prior knowledge, and the models can be iteratively optimized with the expectation that optimization will settle to some optimal maximum or minimum solution. Once it is known what the user is doing, the proper characteristics of the neural activity and proper models can be queried. The data models may be layered or staged, so that, e.g., a first model focuses on pre-processing data (e.g., filtering), the next model focuses on clustering the pre-processed data to separate certain features that may be recognized to correlate with a known activity performed by the user, and then the next model can query a separate model to determine the mental state based on that user activity.

As will be described in further detail below, the training data or prior knowledge of the user may be obtained by providing known life/work context to the user. Altogether, the models can be used to track mental state and perception under natural or quasi-natural (i.e., in response to providing known life/work context to the user) and dynamic conditions taking in the time-course of averaged activity and determining the mental state of the user based on constant or spontaneous fluctuations in the characteristics of the brain activity extracted from the data.

A set of data models that have already been proven, for example in a laboratory setting, can be initially uploaded to the non-invasive anti-priming system 10, which system will then use the uploaded data models to determine the mental state of the user. Optionally, the non-invasive anti-priming system 10 may collect data during actual use with the user, which can then be downloaded and analyzed in a separate server, for example in a laboratory setting, to create new or updated data models. Software upgrades, which may include the new or updated models, can be uploaded to the non-invasive anti-priming system 10 to provide new or updated data modelling and data collection.

Further details regarding determining the mental state of a person based on detected brain activity can be found in a variety of peer-reviewed publications. See, e.g., Lee, B. T., Seok, J. H., Lee., B. C, Cho, S. W., Chai, J. H., Choi, I. G., Ham, B. J., "Neural correlates of affective processing in response to sad and angry facial stimuli in patients with major depressive disorder," *Prog Neuropsychopharmacol Biol Psychiatry*, 32(3), 778-85 (2008); A. C. Felix-Ortiz, A. G., Burgos-Robles, A., Bhagat, N. D., Leppla, C. A., Tye, K. M., "Bidirectional modulation of anxiety-related and social behaviors by amygdala projections to the medial prefrontal cortex," *Neuroscience* 321, 197-209 (2016); Beauregard, M., Levesque, J. & Bourgouin, P., "Neural correlates of conscious self-regulation of emotion," *J. Neurosci.* (2001): 21, RC165; Phan, K. L., Wager, T., Taylor, S. F. & Liberzon, I., "Functional neuroanatomy of emotion: a meta-analysis of emotion activation studies in PET and fMRI," *Neuroimage,* 16, 331-348 (2002); Canli, T. & Amin, Z., "Neuroimaging of emotion and personality: scientific evidence and ethical considerations," *Brain Cogn.,* 50, 414-431 (2002), McCloskey, M. S., Phan, K. L. & Coccaro, E. F., "Neuroimaging and personality disorders," *Curr. Psychiatry Rep.,* 7, 65-72 (2005); Heekeren, H. R., Marrett, S., Bandettini, P. A. & Ungerleider, L. G., "A general mechanism for perceptual decision-making in the human brain," *Nature,* 431, 859-862 (2004); Shin L M, Rauch S L, Pitman R K. Amygdala, Medial Prefrontal Cortex, and Hippocampal Function in PTSD, *Ann N Y Acad Sci.,* 1071(1) (2006); Lis E, Greenfield B, Henry M, Guile J M, Dougherty G., "Neuroimaging and genetics of borderline personality disorder: a review," *J Psychiatry Neurosci.,* 32(3), 162-173 (2007); Etkin A, Wager T D, "Functional neuroimaging of anxiety: a meta-analysis of emotional processing in PTSD, social anxiety disorder, and specific phobia," *Am J Psychiatry,* 164(10), 1476-1488 (2007); Etkin A. Functional Neuroimaging of Major Depressive Disorder: A Meta-Analysis and New Integration of Baseline Activation and Neural Response Data, *Am J Psychiatry,* 169(7), 693-703 (2012); Sheline Y I, Price J L, Yan Z, Mintun M A, "Resting-state functional MRI in depression unmasks increased connectivity between networks via the dorsal nexus, *Proc Natl Acad Sci.,* 107(24), 11020-11025 (2010); Bari A, Robbins T W, "Inhibition and impulsivity: Behavioral and neural basis of response control," *Prog Neurobiol.,* 108:44-79 (2013); Kagias, Konstantinos et al. "Neuronal responses to physiological stress," *Frontiers in genetics,* 3:222 (2012).

The non-invasive anti-priming system 10 also optionally comprises a database, server, or cloud structure 16 configured for tracking the brain activity of the user 12. For example, the database, server, or cloud structure 16 may be configured to collect raw data (e.g., brain activity data) generated by the brain interface assembly 14. Furthermore, the database, server, or cloud structure 16 (independently of or in conjunction with the mental state determination functions of the brain interface assembly 14) may be configured for performing a data analysis of the raw data in order to determine whether the user 12 is currently being primed.

For example, if the raw data obtained by the user 12 is being anonymized and stored in the database, server, or cloud structure 16, the data models can be pooled across various users, which deep learning algorithms would benefit from. The database, server, or cloud structure 16 may be configured for performing cross-correlation analysis of the signal data analysis in order to reduce the pool size of the database and focus subject averaged data to a pool that is similar to the user. Most likely, each user will have a portion of their model optimized to them, but then another portion takes advantage of patterns extracted from a larger pool of users. It should also be appreciated that each user may perform any variety of an infinite number of activities that expose the user to various priming effects. Thus, even if a user is properly calibrated, such calibration will only be for a small set of infinite possibilities. Generalizing models may comprise various variabilities and optimizing may be difficult. However, by building a large user database on the database, server, or cloud structure 16, a data analysis pipeline connected to such database, server, or cloud structure 16 can preprocess data (clean it up), extract all different kinds of features, and then apply an appropriate data model, to overcome this issue. The brain activity of the user 12 may be tracked with additional life/work context to acquire meta data in depth assessment of awareness and behavior modulation patterns of the user 12. Although, all of the tracked data analysis has been described as being performed by the database, server, or cloud structure 16, it should be appreciated that at least a portion of the tracked data analysis functionality may be incorporated in another suitable device, e.g., the biofeedback assembly 18 described in further detail below, with the caveat that it is preferred that the tracking of the brain activity between a pool of users be performed by the database, server, or cloud structure 16.

The non-invasive anti-priming system 10 further comprises a biofeedback assembly 18 that serves as input through one or more of the various nervous systems of the user 12, thereby closing the loop that connects the user's 12 subconscious mental state via brain interfaces (as described more fully below) by the brain interface assembly 14 to the user's 12 conscious awareness of being primed by an external stimulus.

To this end, the biofeedback assembly 18, in response to a determination that the user 12 is currently being primed, is configured for automatically alerting the user 12 that he or she is currently being primed. In addition to alerting the user 12 that he or she is currently being primed, the biofeedback assembly 18 may be further configured for communicating the urgency, levels of priming, and other user-relevant information to the user 12.

In the embodiment illustrated in FIG. 1A, the biofeedback assembly 18 takes the form of a non-wearable peripheral device (e.g., a Smartphone, tablet computer, or the like) providing audio or visual signals to the user 12 (e.g., in the form of an audio or visual alert), and thus serves as brain input to the user 12 through the auditory or visual nervous system. Such biofeedback assembly 18 may be further configured for incorporating life/work context (e.g., GPS tracking, calendar scheduling, means for listening to music, means for listening to a lecture, means for learning a language, means for engaging in video conversations with others located in remote locations, means for surfing the world-wide-web, etc.) into the experience of the user 12. Thus, in this case, instead of originating from an external source, such as a television or radio, priming from an external stimulus may actually originate from the biofeedback assembly 18, itself.

The biofeedback assembly 18 is further configured for, in response to a determination that the user 12 is currently being primed by an external stimulus, automatically presenting interactive neural feedback to the user 12 in a manner that modulates the mental state of the user 12. As one example, if the user 12 has a negative mental state (e.g., fear or anxiety) as a result of being primed by the external stimulus, the mental state of the user 12 may be modulated by the biofeedback assembly 18 to promote a positive mental state of the user 12 (e.g., joy or relaxation).

One or more negative mental states and/or one or more positive mental states can be programmed into the biofeedback assembly 18, such that the non-invasive brain interface assembly 14 may focus on the programmed negative state(s) when analyzing the brain activity of the user 12, and the biofeedback assembly 18 presents neural feedback to the user 12 in a manner that promotes the programmed positive mental state(s) in the user 12. Such mental state(s) of the user 12 can be individually programmed using a manual selection or manual input on the biofeedback assembly 18 by the user 12, and can be made available through the graphical user interface of the biofeedback assembly 18 though a button, tab, or icon, e.g., through the use of a radio button or similar selectable options, representing one of a set of options of individual experiences.

In one example, anxiety and relaxation may be programmed into the biofeedback assembly 18, such that the non-invasive brain interface assembly 14 focuses on the mental state of anxiety when analyzing the brain activity of the user 12, and the biofeedback assembly 18 presents the neural feedback to the user 12 in a manner that promotes the mental state of relaxation in the user 12.

In another embodiment, such positive mental state may be a cognitive state encompassing intellectual functions and processes, such as, e.g., memory retrieval, focus, attention, creativity, reasoning, problem solving, decision making, comprehension and production of language education, etc. The goal of this embodiment, in response to determining that the user 12 is being primed, is to maintain the user 12 within the cognitive state (where better objective decision-making can be made and/or maximize production of the user 12 within a work environment), while preventing the user 12 from slipping into a negative and counterproductive emotional state. It should be appreciated that maintaining the user 12 within a cognitive state does not mean that the user 12 will be devoid of any emotion, but rather such user 12 will tend to use transient emotions as information, and will not dwell on any particular negative emotion.

In the preferred embodiment, the biofeedback assembly 18 is configured for presenting the neural feedback (e.g., visually or aurally) in the form of one or more training sessions to the user 12. Such training session(s) may include learning tools, e.g., instructional media (e.g., video or audio) providing instructions to the user promoting a positive mental state to counteract the negative priming. For example, if the brain interface assembly 14 detects that the user 12 is feeling anxious in response to priming, the biofeedback assembly 18 may present a training session that provides suggestions on how to reduce anxiety to the user 12. As another example, the training session can comprise a request for the user 12 to perform a mental exercise the promotes a positive mental state. For example, such exercise can be a relaxation exercise (e.g., changing a visual stimulus from red to green by relaxing his or her mind), with the exercise being terminated when the mental state of the user 12 has been determined to fully transition from anxiety to relaxation, e.g., when the ratio of frequency bands associated with anxiety versus relaxation has sufficiently flipped form anxiety to relaxation.

In one embodiment, the biofeedback assembly 18 is configured for modifying the neural feedback presented to the user 12 by presenting a list of training sessions to the user 12 that promote the positive mental state of the user 12 in response to determining that the user 12 is being primed by an external stimulus, as illustrating in FIG. 2A. The biofeedback assembly 18 may comprise different training session lists respectively corresponding to different positive mental states to be promoted (e.g., relaxation, joy, cognitive, etc.). The training session lists may be pre-generated (i.e., before the first training session in each list is presented to the user 12) or may be dynamically generated, e.g., training sessions may be incorporated into the respective training session list after the first training session in that list is presented to the user 12.

The biofeedback assembly 18 may be configured for customizing each training session list for the user 12, such that when the user 12 receives and processes the neurofeedback, each training session changes how the brain of the user 12 resonates. For example, the biofeedback assembly 18 may be configured for selecting different training sessions to be provided to the user 12, and for ultimately determining the best training sessions that promote the desired mental state(s) programmed into the biofeedback assembly 18. The biofeedback assembly 18 may be further configured for repeatedly validating the best training sessions to ensure that they continue to promote the desired mental state(s) of the user 12.

In this case, while the biofeedback assembly 18 presents a series of training sessions to the user 12, the non-invasive brain interface assembly 14 may be configured for detecting brain activity of the user 12 and determining the mental state of the user 12. The biofeedback assembly 18 may be configured for automatically modifying a training session list based on the determined mental state of the user 12 for each particular training session.

For example, if the determined mental state matches the desired positive mental state to which the training session list corresponds (e.g., the positive mental state programmed into the biofeedback assembly 18), the biofeedback assembly 18 may be configured for automatically modifying the training session list that promotes the mental state of relaxation to retain the tagged (i.e., selected) training session in that training session list (in this case Training Session 1), as illustrated in FIG. 2B. In contrast, if the determined mental state does not match the desired positive mental state to which the training session list corresponds, the biofeedback assembly 18 may be configured for automatically modifying the training session list that promotes the mental state of relaxation to discard the tagged training session, e.g., Training Session 1, from the training session list, as illustrated in FIG. 2C.

Furthermore, if the determined mental state matches the desired positive mental state to which the training session list corresponds, the biofeedback assembly 18 may not only be configured for retaining the tagged training session in the training session list, the biofeedback assembly 18 may be configured for including more training sessions in the training session list having the same attributes as the tagged training session that matches the desired positive mental state to which the training session list corresponds (in this case, Training Sessions 6-8), as illustrated in FIG. 2D, and if the determined mental state does not match the desired positive mental state to which the training session list corresponds, biofeedback assembly 18 may not only be configured for discarding the tagged training session from the training session list, the biofeedback assembly 18 may be configured for including less training sessions in the training session list having the same attributes as the tagged training session that does not match the desired positive mental state to which the training session list corresponds (in this case, deleting Training Sessions 1, 2 and 4), as illustrated in FIG. 2E.

The brain interface assembly 14 can be configured for determining whether current mental state of the user 12 matches the desired mental state based on certain criteria, e.g., if the anxiety of the user 12 is reduced by a certain amount compared to a baseline amount of anxiety, to determine the effectiveness of any given training session. For example, if brain interface assembly measures the ratio of certain frequency bands associated with anxiety versus relaxation to determine the mental state of the user 12 with respect to anxiety/relaxation, a match between the current mental state of the user 12 and the desired mental state of the user 12 may be determined to occur when the ratio is above or below or certain pre-determined value.

It should be appreciated that although the biofeedback assembly 18 has been described as performing the processing necessary for modifying the neural feedback presented to the user in a manner that modulates the mental state of the user 12, such processing can be performed external to the biofeedback assembly 18, e.g., in the processor and computing means of the non-invasive brain interface assembly 14.

Furthermore, although the biofeedback assembly 18 has been described as a single device, the functionalities of the biofeedback assembly may be performed by separate devices. For example, as illustrated in FIG. 1B, a biofeedback assembly 18' may comprise a non-wearable peripheral biofeedback device 18a and a wearable biofeedback device 18b. The non-wearable peripheral biofeedback device 18a is configured presenting this interactive neural feedback to the user 12 in much the same manner as the biofeedback assembly 18 described above with respect to FIG. 1A. The wearable biofeedback device 18b is specially designed to be worn by the user 12, and is configured for providing/directing vibrational (or haptic) signals through peripheral somatosensation, e.g., to areas of the user's 12 skin, e.g., arm, wrist, hand, finger, etc., to alert the user 12 that he or she is currently being primed.

In this manner, instead of serving as a brain input to the user 12 through the auditory or visual nervous system, as discussed above with respect to FIG. 1A, the wearable biofeedback device 18b serves as a brain input to the user 12 through the peripheral nervous (PNS) or sympathetic nervous system (SNS). The biofeedback device 18b may encode different messages by how the vibrations are constructed or modulated in amplitude or frequency. In one embodiment, the vibrations encode speech, e.g., conversations or speech envelopes, or encode speech at a word level, e.g., single vowel, single word, or a combination of single words and vowels. In another embodiment, the vibration modalities may be encoded to mental state type, level, urgency, or other user-relevant information.

Thus, it can be appreciated that the biofeedback assembly can be a single peripheral device (e.g., the biofeedback assembly 18 illustrated in FIG. 1A), which provides both the functionality of alerting the user 12 that he or she is currently being primed, and the functionality of presenting interactive neural feedback to the user 12 in a manner that modulates the mental state of the user 12, or may comprise multiple devices (e.g., the non-wearable peripheral biofeedback device 18a and wearable biofeedback device 18b of the biofeedback assembly 18' illustrated in FIG. 1B), which separately provide the functionalities of alerting the user 12 that he or she is currently being primed and presenting interactive neural feedback to the user 12 in a manner that modulates the mental state of the user 12.

Figure 3:
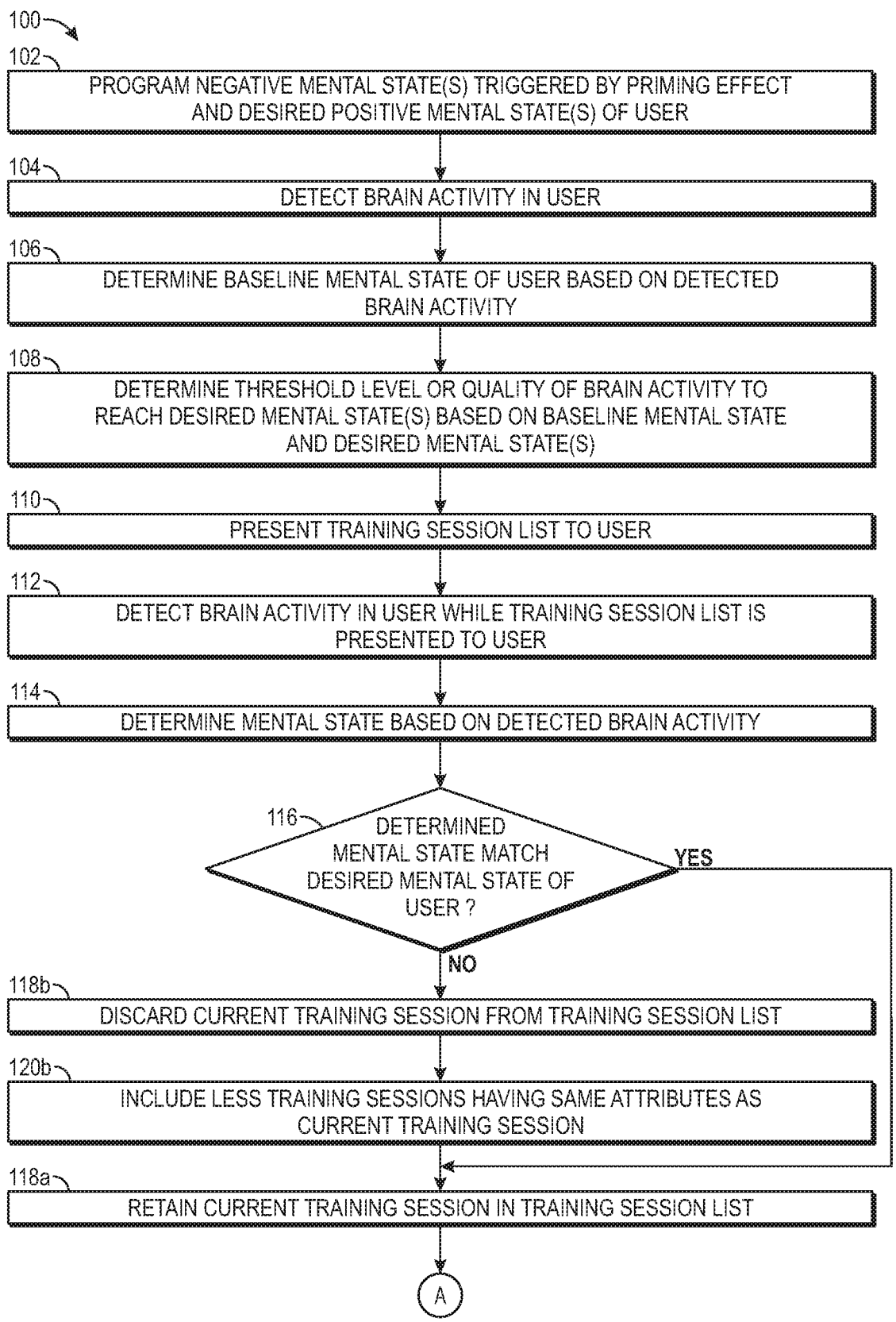
FIG. 3 is a flow diagram illustrating one method of operating the non-invasive anti-priming system of FIGS. 1A and 1B.
Figure 3:
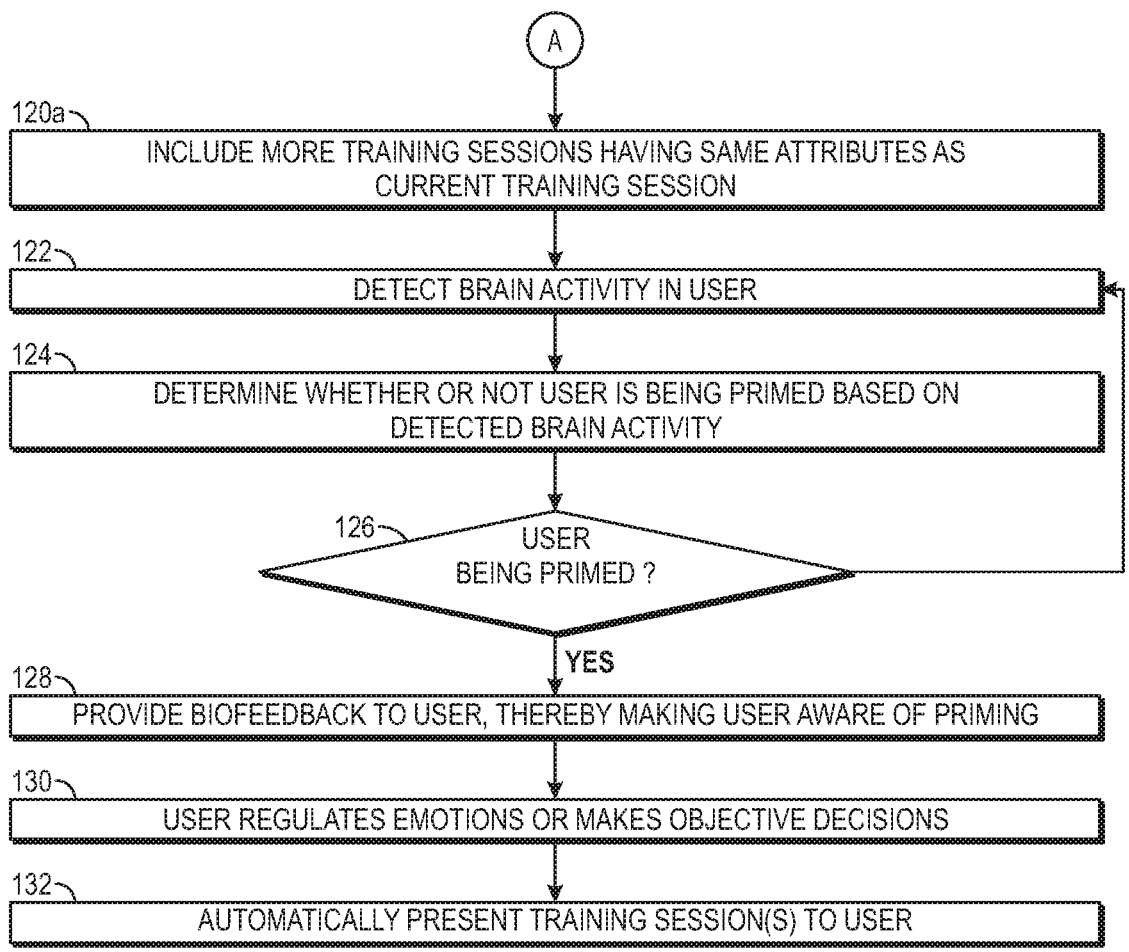

Having described the structure, function, and application of data models of the non-invasive anti-priming system 10, one method 100 of operating the non-invasive anti-priming system 10 will now be described with reference to FIG. 3.

Initially, the user 12 programs the biofeedback assembly 18 (or 18') with the negative mental state(s) that presumably is triggered by the priming effect (e.g., fear or anxiety), as well as the desired mental state or mental states (e.g., relaxation, joy, cognitive, etc.) that counteract the priming effect (step 102).

The brain interface assembly 14 is then calibrated with a baseline mental state of the user 12. In particular, the brain interface assembly 14 first detects the brain activity of the user 12 (step 104). For example, the brain interface assembly 14 may detect energy (e.g., optical energy or magnetic energy) from the brain and through the skull of the user 12, and determine the brain activity in response to detecting the energy from the brain of the user 12. The brain interface assembly 14 (or alternatively, the biofeedback assembly 18 (or 18') or database, server, or cloud structure 16) then determines a baseline mental state of the user 12 based on the detected brain activity (step 106).

The brain interface assembly 14 (or alternatively, the biofeedback assembly 18 (or 18')) then performs an analysis of the baseline mental state of the user 12 and the desired mental state(s) of the user 12 (step 108). In this manner, the brain interface assembly 14 can be calibrated to the desired mental state(s) of the user 12, such that a threshold level or quality of the brain activity of the user 12 corresponding to the desired mental state(s) can be determined. Thus, the user 12 will be determined to have reached the mental state(s) only after the detected brain activity of the user 12 has exceeded the threshold level or quality. Steps 104-108 may be periodically performed to ensure that the brain interface assembly 14 remains calibrated to the baseline state of the user 12, which may change over time.

Next, the biofeedback assembly 18 (or 18') generates and customizes training session lists for the user 12. In particular, the biofeedback assembly 18 (or 18') presents a list of training sessions to the user 12 (step 110). The brain interface assembly 14 detects the brain activity of the user 12 while each training session in the training session list is presented to the user 12 (step 112). For example, the brain interface assembly 14 may detect energy (e.g., optical energy or magnetic energy) from the brain and through the skull of the user 12, and determine the brain activity in response to detecting the energy from the brain of the user 12. The brain interface assembly 14 (or alternatively, the database, server, or cloud structure 16) then determines, based on the detected brain activity, a mental state of the user 12 (step 114).

If the determined mental state matches the desired mental state to which the training session list corresponds (step 116), the biofeedback assembly 18 (or 18') automatically retains the currently presented tagged training session in the training session list (step 118a), and includes more training sessions having the same attributes as the currently presented tagged training session in the training session list (step 120a). In contrast, if the determined mental state does not match the desired mental state to which the training session list corresponds (step 116), the biofeedback assembly 18 (or 18') automatically discards the currently presented tagged training session from the training session list (step 118b), and includes less training sessions having the same attributes as the currently presented tagged training session in the training session list (step 120b).

Once the biofeedback assembly 18 (or 18') is programmed with the training session list(s), the non-invasive anti-priming system 10 detects whether or not the user 12 is being primed by detecting one of the negative mental state(s) programmed into the biofeedback assembly 18 (or 18'), and if priming is detected, the user takes a corrective action to ensure that the user 12 does not fall prey to the priming.

In particular, the brain interface assembly 14 then detects the brain activity of the user 12 (step 122). The brain interface assembly 14 (or alternatively, the biofeedback assembly 18 (or 18') or database, server, or cloud structure 16) then determines whether or not the user 12 is being primed by an external stimulus based on the detected brain activity (step 124). If it is determined that the user 12 is being primed by an external stimulus (step 126), the biofeedback assembly 18 (or wearable biofeedback device 18b of the biofeedback assembly 18') provides biofeedback to the user 12, thereby alerting the user 12 that he or she is being primed (block 128).

For example, the biofeedback assembly 18 (FIG. 1A) may provide audio or visual signals to the user 12 through the auditory or visual nervous system of the user 12, or the wearable biofeedback device 18b of the biofeedback assembly 18' (FIG. 1B) may provide/direct vibrational signals to the user 12 through peripheral somatosensation, e.g., vibrational signals encoded with one or more messages. Thus, input is provided to the brain of the user 12 to alert the user 12 that he or she is being primed by an external stimulus. As such, the user 12 may regulate, adjust, and/or calibrate his or her emotions or make more objective decisions (step 130). Furthermore, the biofeedback assembly 18 (FIG. 1A) or the non-wearable peripheral biofeedback device 18a of the biofeedback assembly 18' (FIG. 1B) may automatically present one or more training sessions contained in the training session list to which the programmed mental state corresponds, thereby promoting the desired mental state of the user 12 (step 132). If it is determined that the user 12 is not being primed by an external stimulus (step 126), the anti-priming system 10 returns to step 122, and the process repeats.

Figure 4:
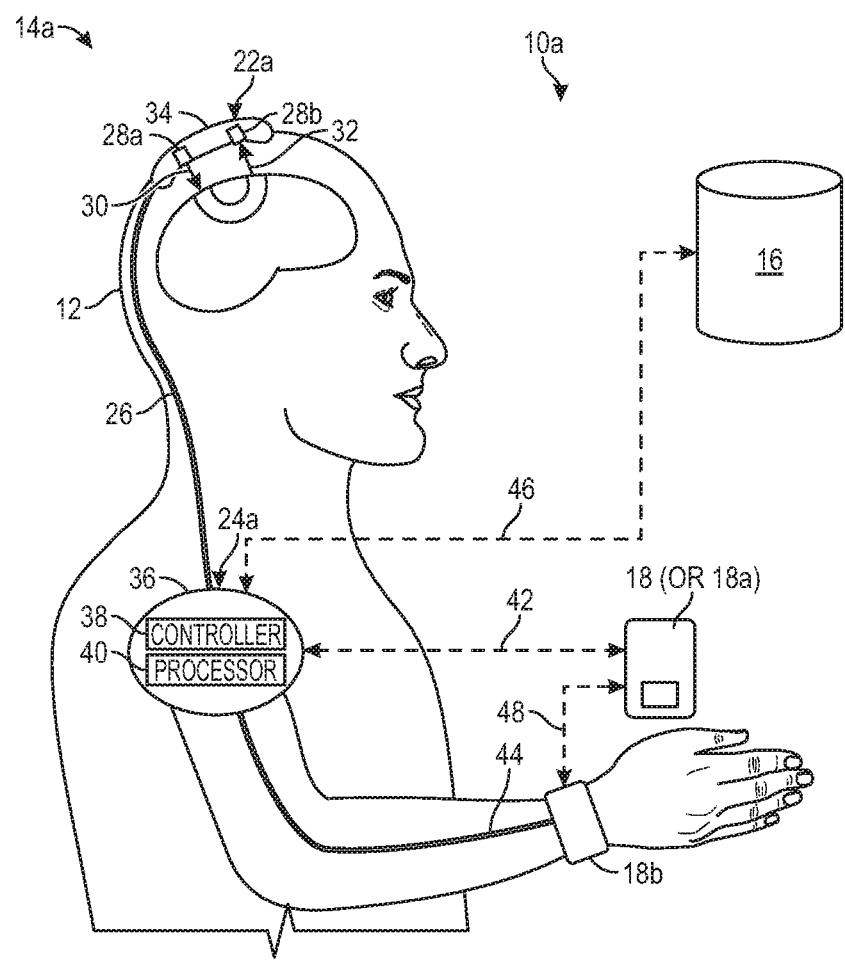
FIG. 4 is a view of one specific embodiment of the non-invasive anti-priming system of FIGS. 1A and 1B.

Referring to FIG. 4, one particular embodiment of an anti-priming system 10a will now be described. The non-invasive anti-priming system 10a comprises an optically-based non-invasive brain interface assembly 14a, which may, e.g., incorporate any one or more of the neural activity detection technologies described in U.S. patent application Ser. No. 15/844,370, entitled "Pulsed Ultrasound Modulated Optical Tomography Using Lock-In Camera" (now U.S. Pat. No. 10,335,036), U.S. patent application Ser. No. 15/844,398, entitled "Pulsed Ultrasound Modulated Optical Tomography With Increased Optical/Ultrasound Pulse Ratio" (now U.S. Pat. No. 10,299,682), U.S. patent application Ser. No. 15/844,411, entitled "Optical Detection System For Determining Neural Activity in Brain Based on Water Concentration" (now U.S. Pat. No. 10,420,469), U.S. patent application Ser. No. 15/853,209, entitled "System and Method For Simultaneously Detecting Phase Modulated Optical Signals" (now U.S. Pat. No. 10,016,137), U.S. patent application Ser. No. 15/853,538, entitled "Systems and Methods For Quasi-Ballistic Photon Optical Coherence Tomography In Diffusive Scattering Media Using a Lock-In Camera" (now U.S. Pat. No. 10,219,700), U.S. patent application Ser. No. 16/266,818, entitled "Ultrasound Modulating Optical Tomography Using Reduced Laser Pulse Duration," U.S. patent application Ser. No. 16/299,067, entitled "Non-Invasive Optical Detection Systems and Methods in Highly Scattering Medium," U.S. patent application Ser. No. 16/379,090, entitled "Non-Invasive Frequency Domain Optical Spectroscopy For Neural Decoding," U.S. patent application Ser. No. 16/382,461, entitled "Non-Invasive Optical Detection System and Method," U.S. patent application Ser. No. 16/392,963, entitled "Interferometric Frequency-Swept Source And Detector In A Photonic Integrated Circuit," U.S. patent application Ser. No. 16/392,973, entitled "Non-Invasive Measurement System and Method Using Single-Shot Spectral-Domain Interferometric Near-Infrared Spectroscopy Based On Orthogonal Dispersion, U.S. patent application Ser. No. 16/393,002, entitled "Non-Invasive Optical Detection System and Method Of Multiple-Scattered Light With Swept Source Illumination," U.S. patent application Ser. No. 16/385,265, entitled "Non-Invasive Optical Measurement System and Method for Neural Decoding," U.S. patent application Ser. No. 16/533,133, entitled "Time-Of-Flight Optical Measurement And Decoding Of Fast-Optical Signals," U.S. patent application Ser. No. 16/565,326, entitled "Detection Of Fast-Neural Signal Using Depth-Resolved Spectroscopy," U.S. patent application Ser. No. 16/226,625, entitled "Spatial and Temporal-Based Diffusive Correlation Spectroscopy Systems and Methods," U.S. Provisional Patent Application Ser. No. 62/772,584, entitled "Diffuse Correlation Spectroscopy Measurement Systems and Methods," U.S. patent application Ser. No. 16/432,793, entitled "Non-Invasive Measurement Systems with Single-Photon Counting Camera," U.S. Provisional Patent Application Ser. No. 62/855,360, entitled "Interferometric Parallel Detection Using Digital Rectification and Integration", U.S. Provisional Patent Application Ser. No. 62/855,380, entitled "Interferometric Parallel Detection Using Analog Data Compression," U.S. Provisional Patent Application Ser. No. 62/855,405, entitled "Partially Balanced Interferometric Parallel Detection," which are all expressly incorporated herein by reference.

The brain interface assembly 14a includes a wearable unit 22a configured for being applied to the user 12, and in this case, worn on the head of the user 12; and an auxiliary head-worn or non-head-worn unit 24a (e.g., worn on the neck, shoulders, chest, or arm). Alternatively, the functionality of the unit 24a may be incorporated into the head-worn unit 22a. The auxiliary non-head-worn unit 24a may be coupled to the head-worn unit 22a via a wired connection 26 (e.g., electrical wires). Alternatively, the brain interface assembly 14a may use a non-wired connection (e.g., wireless radio frequency (RF) signals (e.g., Bluetooth, Wifi, cellular, etc.) or optical links (e.g., fiber optic or infrared (IR)) for providing power to or communicating between the respective head-worn unit 22a and the auxiliary unit 24a.

The head-worn unit 22a comprises electronic or optical components, such as, e.g., one or more optical sources, an interferometer, one or more optical detector(s) (not shown), etc., an output port 28a for emitting sample light 30 generated by the brain interface assembly 14a into the head of the user 12, an input port 28b configured for receiving neural-encoded signal light 32 from the head of the user 12, which signal light is then detected, modulated and/or processed to determine neural activity within the brain of the user 12, and a support housing structure 34 containing the electronic or optical components, and ports 28a, 28b.

The support housing structure 34 may be shaped, e.g., have a banana, headband, cap, helmet, beanie, other hat shape, or other shape adjustable and conformable to the user's head, such that the ports 28a, 28b are in close contact with the outer skin of the head, and in this case, the scalp of the user 12. The support housing structure 34 may be made out of any suitable cloth, soft polymer, plastic, hard shell, and/or any other suitable material as may serve a particular implementation. In an alternative embodiment, optical fibers (not shown) may be respectively extended from the ports 28a, 28b, thereby freeing up the requirement that the ports 28a, 28b be disposed in close proximity to the surface of the head. In any event, an index matching fluid may be used to reduce reflection of the light generated by the head-worn unit 22a from the outer skin of the scalp. A strap, or belt (not shown) can be used to secure the support housing structure 34 to the head of the user 12.

The auxiliary unit 24a comprises a housing 36 containing a controller 38 and a processor 40. The controller 38 is configured for controlling the operational functions of the head-worn unit 22a, whereas the processor 40 is configured for processing the neural-encoded signal light 32 acquired by the head-worn unit 22a to detect and localize the neural activity within the brain of the user 12. The auxiliary unit 24a may additionally include a power supply (which if head-worn, may take the form of a rechargeable or non-chargeable battery), a control panel with input/output functions, a display, and memory. Alternatively, power may be provided to the auxiliary unit 24a wirelessly (e.g., by induction).

The functionalities of the database, server, or cloud structure 16 and biofeedback assembly 18 (or 18') may be the same as described above with respect to FIGS. 1A and 1B.

The biofeedback assembly 18 (or the non-wearable peripheral biofeedback device 18a of the biofeedback assembly 18') is coupled to the auxiliary unit 24a of the brain interface assembly 14a via a wireless connection 42 (e.g., wireless radio frequency (RF) signals (e.g., Bluetooth, Wifi, cellular, etc.) or optical links (e.g., fiber optic or infrared (IR)) for communicating between the biofeedback assembly 18 and the brain interface assembly 14a (and/or the biofeedback assembly 18). Alternatively, a wired connection between the biofeedback assembly 18 (or the non-wearable peripheral biofeedback device 18a of the biofeedback assembly 18') and the brain interface assembly 14a may be used.

The wearable biofeedback device 18b of the alternative biofeedback assembly 18' is coupled to the brain interface assembly 14a (and in this case, to the auxiliary unit 24a) via a wired connection 44 (e.g., electrical wires). Alternatively, a non-wired connection (e.g., wireless radio frequency (RF) signals (e.g., Bluetooth, Wifi, cellular, etc.) or optical links (e.g., fiber optic or infrared (IR)) for providing power to or communicating between the respective the auxiliary unit 24a of the brain interface assembly 14a and the alternative wearable biofeedback device 18b of the biofeedback assembly 18' may be used. The non-wearable peripheral biofeedback device 18a and wearable biofeedback device 18b may be coupled to each other via a wired connection (e.g., electrical wires) or a non-wired connection 48 (e.g., wireless radio frequency (RF) signals (e.g., Bluetooth, Wifi, cellular, etc.) or optical links (e.g., fiber optic or infrared (IR)), for providing power to or communicating therebetween.

The database, server, or cloud structure 16 may be coupled to the auxiliary unit 24a of the brain interface assembly 14a (and/or the biofeedback assembly 18 (or 18')) via a wireless connection 46 (e.g., wireless radio frequency (RF) signals (e.g., Bluetooth, Wifi, cellular, etc.) or optical links (e.g., fiber optic or infrared (IR)) for providing power to or communicating between the biofeedback assembly 18 (or 18') and the database, server or cloud structure 16. Alternatively, a wired connection between the database, server, or cloud structure 16 and the auxiliary unit 24a of the brain interface assembly 14a (and/or the biofeedback assembly 18 (or 18')) may be used.

Figure 5:
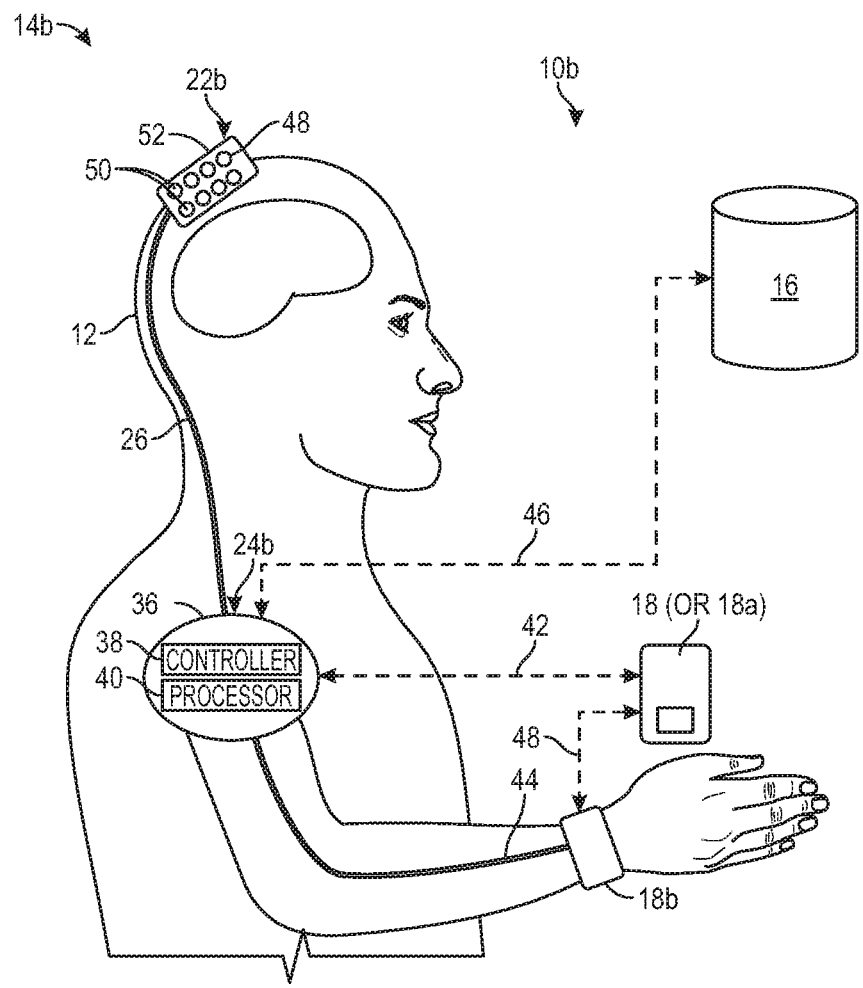
FIG. 5 is a view of another specific embodiment of the non-invasive anti-priming system of FIGS. 1A and 1B.

Referring to FIG. 5, another particular embodiment of an anti-priming system 10b will now be described. The non-invasive anti-priming system 10b comprises an optically-based non-invasive brain interface assembly 14b, which may, e.g., incorporate any one or more of the neural activity detection technologies described in U.S. Non-Provisional patent application Ser. No. 16/051,462, entitled "Fast-Gated Photodetector Architecture Comprising Dual Voltage Sources with a Switch Configuration" (now U.S. Pat. No. 10,158,038), U.S. patent application Ser. No. 16/202,771, entitled "Non-Invasive Wearable Brain Interface Systems Including a Headgear and a Plurality of Self-Contained Photodetector Units Configured to Removably Attach to the Headgear" (now U.S. Pat. No. 10,340,408), U.S. patent application Ser. No. 16/283,730, entitled "Stacked Photodetector Assemblies" (now U.S. Pat. No. 10,515,993), U.S. patent application Ser. No. 16/544,850, entitled "Wearable Systems with Stacked Photodetector Assemblies," U.S. Provisional Patent Application Ser. No. 62/880,025, entitled "Photodetector Architectures for Time-Correlated Single Photon Counting," U.S. Provisional Patent Application Ser. No. 62/889,999, entitled "Photodetector Architectures for Efficient Fast-Gating," U.S. Provisional Patent Application Ser. No. 62/906,620, entitled "Photodetector Systems with Low-Power Time-To-Digital Converter Architectures," U.S. Provisional Patent Application Ser. No. 62/979,866 entitled "Optical Module Assemblies," U.S. Provisional Patent Application Ser. No. 62/992,486 entitled "Laser Diode Driver Circuit with Adjustable Turn-Off and Turn-On Current Slew Rates," U.S. Provisional Patent Application Ser. No. 62/992,491 entitled "Multiplexing Techniques for Interference Reduction in Time-Correlated Signal Photon Counting," U.S. Provisional Patent Application Ser. No. 62/992,493 entitled "SPAD Bias Compensation," U.S. Provisional Patent Application Ser. No. 62/992,497 entitled "Measurement Window Calibration for Detection of Temporal Point Spread Function," U.S. Provisional Patent Application Ser. No. 62/992,499 entitled "Techniques for Determining Impulse Response of SPAD and TDC Systems," U.S. Provisional Patent Application Ser. No. 62/992,502 entitled "Histogram Based Code Density Characterization and Correction in Time-Correlated Single Photon Counting," U.S. Provisional Patent Application Ser. No. 62/992,506 entitled "Selectable Resolution Modes in an Optical Measurement System," U.S. Provisional Patent Application Ser. No. 62/992,510 entitled "Hierarchical Bias Generation for Groups of SPAD Detectors," U.S. Provisional Patent Application Ser. No. 62/992,512 entitled "Detection and Removal of Motion Artifacts in a Wearable Optical Measurement System," U.S. Provisional Patent Application Ser. No. 62/992,526 entitled "Dynamic Range Improvement from Highly Parallel Arrays and SPADs," U.S. Provisional Patent Application Ser. No. 62/992,529 entitled "Single-Photon Avalanche Diode (SPAD) Bias Constant Charge," U.S. Provisional Patent Application Ser. No. 62/992,536 entitled "Calibration of SPAD ToF Systems Based on Per Pixel Dark Count Rate," U.S. Provisional Patent Application Ser. No. 62/992,543 entitled "Estimation of Source-Detector Separation in an Optical Measurement System," U.S. Provisional Patent Application Ser. No. 62/992,550 entitled "Wearable Module for an Optical Measurement or Hybrid Technology Neural Recording System Where the Module Assemblies are Configured for Tiling Multiple Modules Together for Targeted and/or Complete Head Coverage," U.S. Provisional Patent Application Ser. No. 62/992,552 entitled "Wearable Devices for a Brain Computer Interface (BCI) System Where the Wearable Device Includes Conforming Headset Fixation," U.S. Provisional Patent Application Ser. No. 62/992,555 entitled "Integrated Detector Assemblies for a Wearable Module of an Optical Measurement System," U.S. Provisional Patent Application Ser. No. 62/992,559 entitled "Integrated Detector Assemblies for a Wearable Module of an Optical Measurement Where the Detector Assemblies Include Spring Loaded Light Pipes," and U.S. Provisional Patent Application Ser. No. 62/992,567 entitled "Integrated Light Source Assembly with Laser Coupling for a Wearable Optical Measurement System," which are all expressly incorporated herein by reference.

The brain interface assembly 14b includes a head-worn unit 22b that is configured for being applied to the user 12, and in this case, worn on the head of the user 12; and an auxiliary non-head-worn unit 24b (e.g., worn on the neck, shoulders, chest, or arm). Alternatively, the functionality of the unit 24b may be incorporated into the head-worn unit 22b, as described below. The auxiliary non-head-worn unit 24b may be coupled to the head-worn unit 22b via a wired connection 26 (e.g., electrical wires). Alternatively, the brain interface assembly 14b may use a non-wired connection (e.g., wireless radio frequency (RF) signals (e.g., Bluetooth, Wifi, cellular, etc.) or optical links (e.g., fiber optic or infrared (IR)) for providing power to or communicating between the respective head-worn unit 22b and the auxiliary unit 24b.

The head-worn unit 22b includes one or more light sources 48 configured for generating light pulses. The light source(s) 48 may be configured for generating one or more light pulses at one or more wavelengths that may be applied to a desired target (e.g., a target within the brain). The light source(s) 48 may be implemented by any suitable combination of components. For example, light source(s) 48 described herein may be implemented by any suitable device. For example, a light source as used herein may be, for example, a distributed feedback (DFB) laser, a super luminescent diode (SLD), a light emitting diode (LED), a diode-pumped solid-state (DPSS) laser, a laser diode (LD), a super luminescent light emitting diode (sLED), a vertical-cavity surface-emitting laser (VCSEL), a titanium sapphire laser, a micro light emitting diode (mLED), and/or any other suitable laser or light source.

The head-worn unit 22b includes a plurality of photodetector units 50, e.g., comprising single-photon avalanche diodes (SPADs) configured for detecting a single photon (i.e., a single particle of optical energy) in each of the light pulses. For example, an array of these sensitive photodetector units can record photons that reflect off of tissue within the brain in response to application of one or more of the light pulses generated by the light sources 48. Based on the time it takes for the photons to be detected by the photodetector units, neural activity and other attributes of the brain can be determined or inferred.

Photodetector units that employ the properties of a SPAD are capable of capturing individual photons with very high time-of-arrival resolution (a few tens of picoseconds). When photons are absorbed by a SPAD, their energy frees bound charge carriers (electrons and holes) that then become free-carrier pairs. In the presence of an electric field created by a reverse bias voltage applied to the diode, these free-carriers are accelerated through a region of the SPAD, referred to as the multiplication region. As the free carriers travel through the multiplication region, they collide with other carriers bound in the atomic lattice of the semiconductor, thereby generating more free carriers through a process called impact ionization. These new free-carriers also become accelerated by the applied electric field and generate yet more free-carriers. This avalanche event can be detected and used to determine an arrival time of the photon. In order to enable detection of a single photon, a SPAD is biased with a reverse bias voltage having a magnitude greater than the magnitude of its breakdown voltage, which is the bias level above which free-carrier generation can become self-sustaining and result in a runaway avalanche. This biasing of the SPAD is referred to as arming the device. When the SPAD is armed, a single free carrier pair created by the absorption of a single photon can create a runaway avalanche resulting in an easily detectable macroscopic current.

It will be recognized that in some alternative embodiments, the head-worn unit 22b may include a single light source 48 and/or single photodetector unit 50. For example, brain interface system 14b may be used for controlling a single optical path and for transforming photodetector pixel measurements into an intensity value that represents an optical property of a brain tissue region. In some alternative embodiments, the head-worn unit 22b does not include individual light sources. Instead, a light source configured to generate the light that is detected by the photodetector may be included elsewhere in the brain interface system 14b. For example, a light source may be included in the auxiliary unit 24b.

The head-worn unit 22b further comprises a support housing structure 52 containing the light source(s) 48, photodetector units 50, and other electronic or optical components. As will be described in further detail below, the support housing structure 52 may be shaped, e.g., have a banana, headband, cap, helmet, beanie, other hat shape, or other shape adjustable and conformable to the user's head, such that the photodetector units 50 are in close contact with the outer skin of the head, and in this case, the scalp of the user 12. The support housing structure 52 may be made out of any suitable cloth, soft polymer, plastic, hard shell, and/or any other suitable material as may serve a particular implementation.

While brain interface system 14b shows one head-word unit 22b, any suitable number of head-worn units 22b may be used, for instance at different locations on the head.

The auxiliary unit 24b comprises the housing 36 containing the controller 38 and the processor 40. The controller 38 is configured for controlling the operational functions of the head-worn unit 22b, whereas the processor 40 is configured for processing the photons acquired by the head-worn unit 22b to detect and localize the neural activity within the brain of the user 12. The auxiliary unit 24b may additionally include a power supply (which if head-worn, may take the form of a rechargeable or non-chargeable battery), a control panel with input/output functions, a display, and memory. Alternatively, power may be provided to the auxiliary unit 24b wirelessly (e.g., by induction).

The functionalities of the database, server, or cloud structure 16 and biofeedback assembly 18 (or 18') may be the same as described above with respect to FIGS. 1A and 1B.

The biofeedback assembly 18 (or the non-wearable peripheral biofeedback device 18a of the biofeedback assembly 18') is coupled to the auxiliary unit 24b of the brain interface assembly 14b via a wireless connection 42 (e.g., wireless radio frequency (RF) signals (e.g., Bluetooth, Wifi, cellular, etc.) or optical links (e.g., fiber optic or infrared (IR)) for communicating between the biofeedback assembly 18 and the brain interface assembly 14b (and/or the biofeedback assembly 18). Alternatively, a wired connection between the biofeedback assembly 18 (or the non-wearable peripheral biofeedback device 18a of the biofeedback assembly 18') and the brain interface assembly 14b may be used.

The wearable biofeedback device 18b of the alternative biofeedback assembly 18' is coupled to the brain interface assembly 14b (and in this case, to the auxiliary unit 24b) via a wired connection 44 (e.g., electrical wires). Alternatively, a non-wired connection (e.g., wireless radio frequency (RF) signals (e.g., Bluetooth, Wifi, cellular, etc.) or optical links (e.g., fiber optic or infrared (IR)) for providing power to or communicating between the respective the auxiliary unit 24b of the brain interface assembly 14b and the wearable biofeedback device 18b of the alternative biofeedback assembly 18' may be used. The non-wearable peripheral biofeedback device 18a and wearable biofeedback device 18b of the alternative biofeedback assembly 18 may be coupled to each other via a wired connection (e.g., electrical wires) or a non-wired connection 48 (e.g., wireless radio frequency (RF) signals (e.g., Bluetooth, Wifi, cellular, etc.) or optical links (e.g., fiber optic or infrared (IR)), for providing power to or communicating therebetween.

The database, server, or cloud structure 16 may be coupled to the auxiliary unit 24b of the brain interface assembly 14b (and/or the biofeedback assembly 18 (or 18')) via a wireless connection 46 (e.g., wireless radio frequency (RF) signals (e.g., Bluetooth, Wifi, cellular, etc.) or optical links (e.g., fiber optic or infrared (IR)) for providing power to or communicating between the biofeedback assembly 18 (or 18') and the database, server or cloud structure 16. Alternatively, a wired connection between the database, server, or cloud structure 16 and the auxiliary unit 24b of the brain interface assembly 14b (and/or the biofeedback assembly 18 (or 18')) may be used.

Referring now to FIGS. 6A-6D, different embodiments of the brain interface assembly 14b will be described. Such brain interface assemblies 14b may communicate wirelessly or via wire with the biofeedback assembly 18 (or 18'), and database, server, cloud structure 16, as described above. Each of the brain interface assemblies 14b described below comprises a head-worn unit 22b having a plurality of photodetector units 50 and a support housing structure 52 in which the photodetector units 50 are embedded. Each of the photodetector units 50 may comprise, e.g., a SPAD, voltage sources, capacitors, switches, and any other circuit components (not shown) required to detect photons. Each of the brain interface assemblies 14b may also comprise one or more light sources (not shown) for generating light pulses, although the source of such light may be derived from ambient light in some cases. Each of brain interface assemblies 14b may also comprise a control/processing unit 54, such as, e.g., a control circuit, time-to-digital (TDC) converter, and signal processing circuit for controlling the operational functions of the photodetector units 50 and any light source(s), and processing the photons acquired by photodetector units 50 to detect and localize the neural activity within the brain of the user 12. As will be described in further detail below, the control/processing unit 54 may be contained in the head-worn unit 22b or may be incorporated into a self-contained auxiliary unit. As will be set forth below, the support housing structure 52 may be shaped, e.g., have a banana, headband, cap, helmet, beanie, other hat shape, or other shape adjustable and conformable to the user's head, such that the photodetector units 50 are in close contact with the outer skin of the head, and in this case, the scalp of the user 12.

Figure 6A:
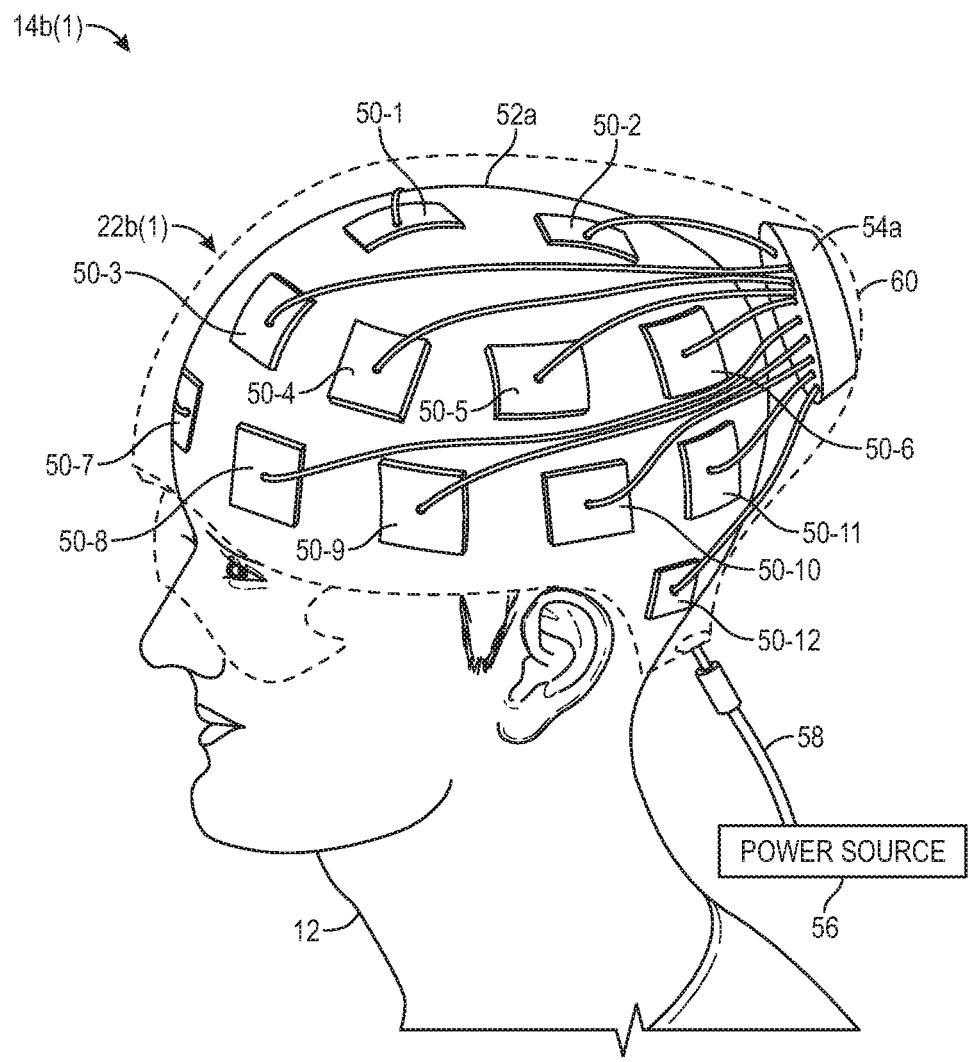
FIG. 6A-6D illustrate exemplary non-invasive wearable devices as used with the system of FIG. 5.

As shown in FIG. 6A, a brain interface assembly 14b(1) comprises a head-worn unit 22b(1) and a power source 56 coupled to the head-worn unit 22b(1) via a power cord 58. The head-worn unit 22b(1) includes the photodetector units 50 (shown as 50-1 through 50-12) and a control/processing unit 54a. The head-worn unit 22b(1) further includes a support housing structure 52a that takes a form of a cap that contains the photodetector units 50 and control/processing unit 54a. The material for the cap 52a may be selected out of any suitable cloth, soft polymer, plastic, hard shell, and/or any other suitable material as may serve a particular implementation. The power source 56 may be implemented by a battery and/or any other type of power source configured to provide operating power to the photodetector units 50, control/processing unit 54a, and any other component included within the brain interface assembly 22b(1) via the power cord 58. The head-worn unit 22b(1) optionally includes a crest or other protrusion 60 formed in the cap 52a for providing means of carrying a control/processing unit 54a.

Figure 6B:
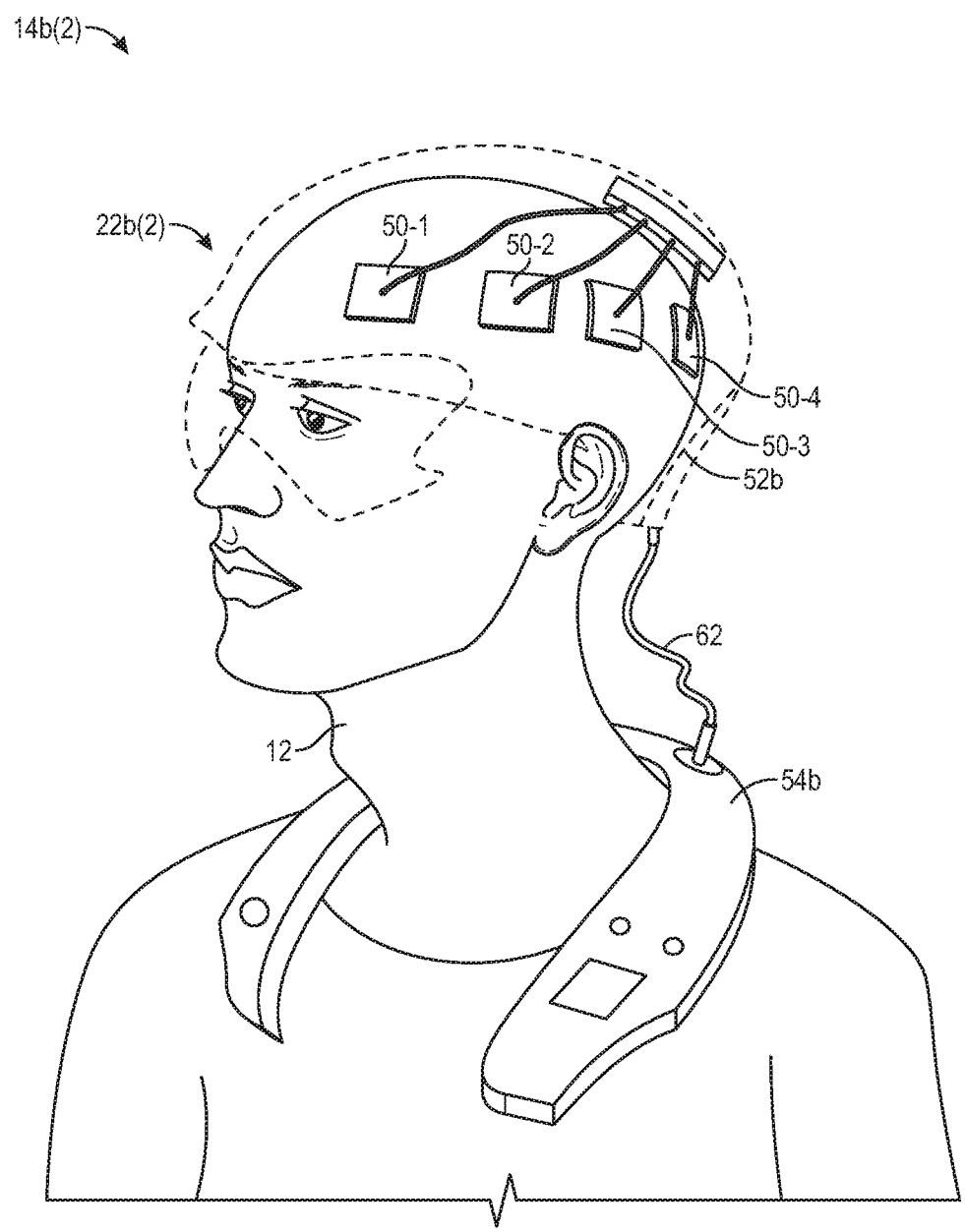

As shown in FIG. 6B, a brain interface assembly 14b(2) comprises a head-worn unit 22b(2) and a control/processing unit 54b coupled to the head-worn unit 22b(2) via a wired connection 62. The head-worn unit 22b(2) includes the photodetector units 50 (shown as 50-1 through 50-4), and a support housing structure 52b that takes a form of a helmet containing the photodetector units 50. The material for the helmet 52b may be selected out of any suitable polymer, plastic, hard shell, and/or any other suitable material as may serve a particular implementation. Unlike the control/processing unit 54a of the brain interface assembly 14b(1) illustrated in FIG. 6A, which is contained in the head-worn unit 22b(1), the control/processing unit 54b is self-contained, and may take the form of a garment (e.g., a vest, partial vest, or harness) for being worn on the shoulders of the user 12. The self-contained control/processing unit 54b may additionally include a power supply (which if head-worn, may take the form of a rechargeable or non-chargeable battery), a control panel with input/output functions, a display, and memory. Alternatively, power may be provided to the self-contained control/processing unit 54b wirelessly (e.g., by induction).

Figure 6C:
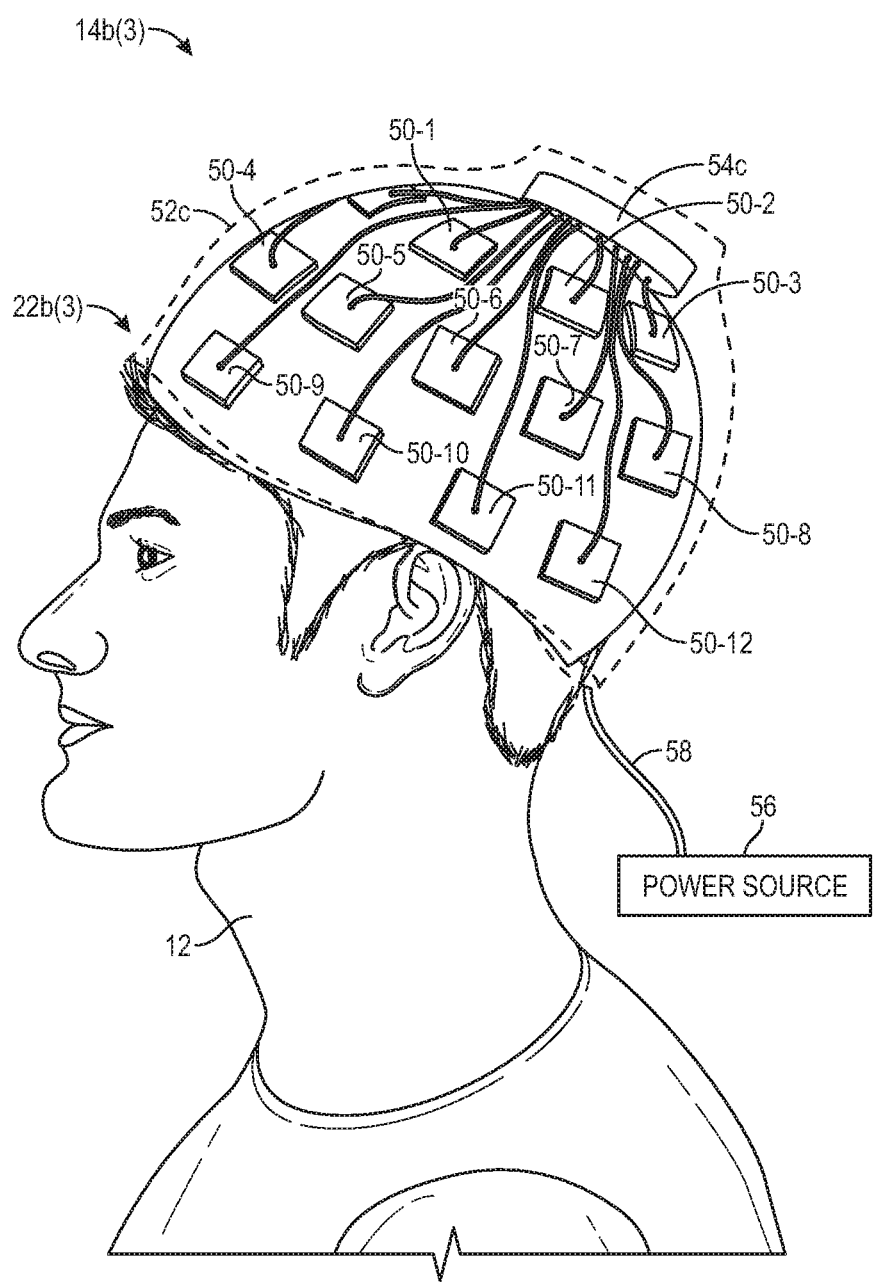

As shown in FIG. 6C, a brain interface assembly 14b(3) comprises a head-worn unit 22b(3) and a power source 56 coupled to the head-worn unit 22b(3) via a power cord 74. The head-worn unit 22b(3) includes the photodetector units 50 (shown as 50-1 through 50-12) and a control/processing unit 54c. The head-worn unit 22b(3) further includes a support housing structure 52c that takes a form of a beanie that contains the photodetector units 50 and control/processing unit 54c. The material for the beanie 68c may be selected out of any suitable cloth, soft polymer, plastic, and/or any other suitable material as may serve a particular implementation. The power source 56 may be implemented by a battery and/or any other type of power source configured to provide operating power to the photodetector units 50, control/processing unit 54c, and any other component included within the brain interface assembly 22b(3) via a wired connection 58.

Figure 6D:
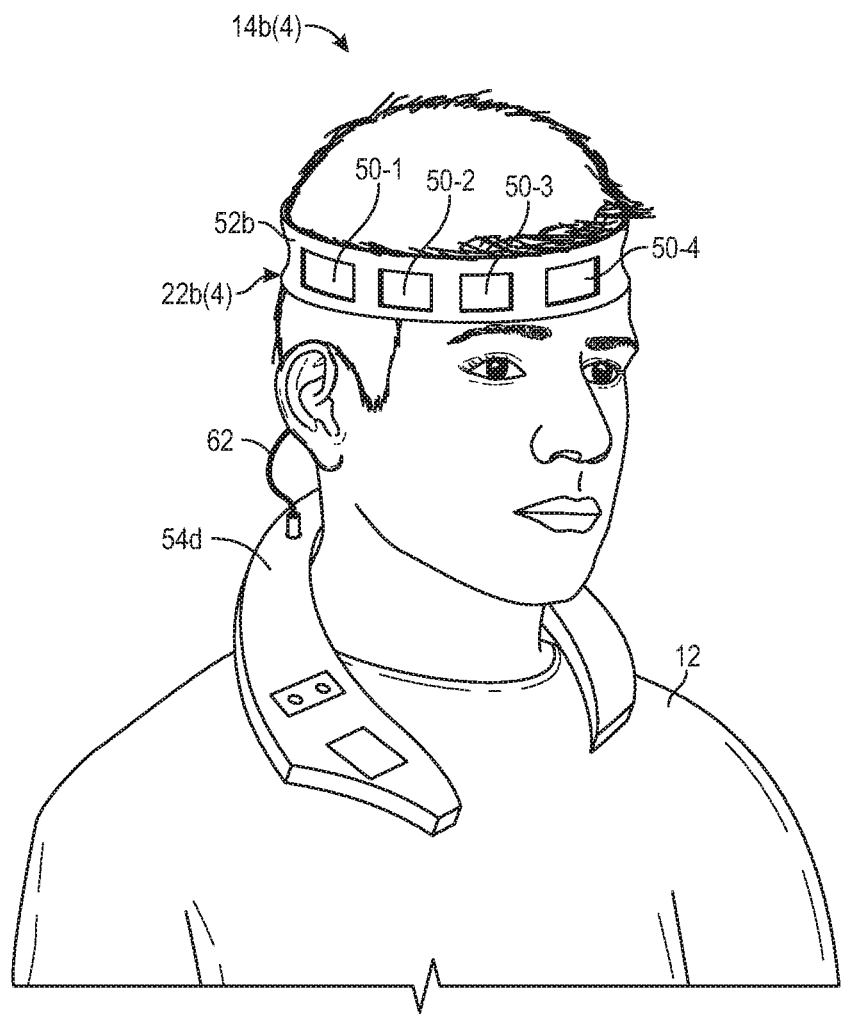

As shown in FIG. 6D, a brain interface assembly 14b(4) comprises a head-worn unit 22b(4) and a control/processing unit 54d coupled to the head-worn unit 22b(4) via a wired connection 62. The head-worn unit 22b(4) includes the photodetector units 50 (shown as 50-1 through 50-4), and a support housing structure 52d that takes a form of a headband containing the photodetector units 50. The material for the headband 52d may be selected out of any suitable cloth, soft polymer, plastic, hard shell, and/or any other suitable material as may serve a particular implementation. The control/processing unit 54d is self-contained, and may take the form of a garment (e.g., a vest, partial vest, or harness) for being worn on the shoulders of the user 12. The self-contained control/processing unit 54d may additionally include a power supply (which if head-worn, may take the form of a rechargeable or non-chargeable battery), a control panel with input/output functions, a display, and memory. Alternatively, power may be provided to the self-contained control/processing unit 54d wirelessly (e.g., by induction).

Figure 7:
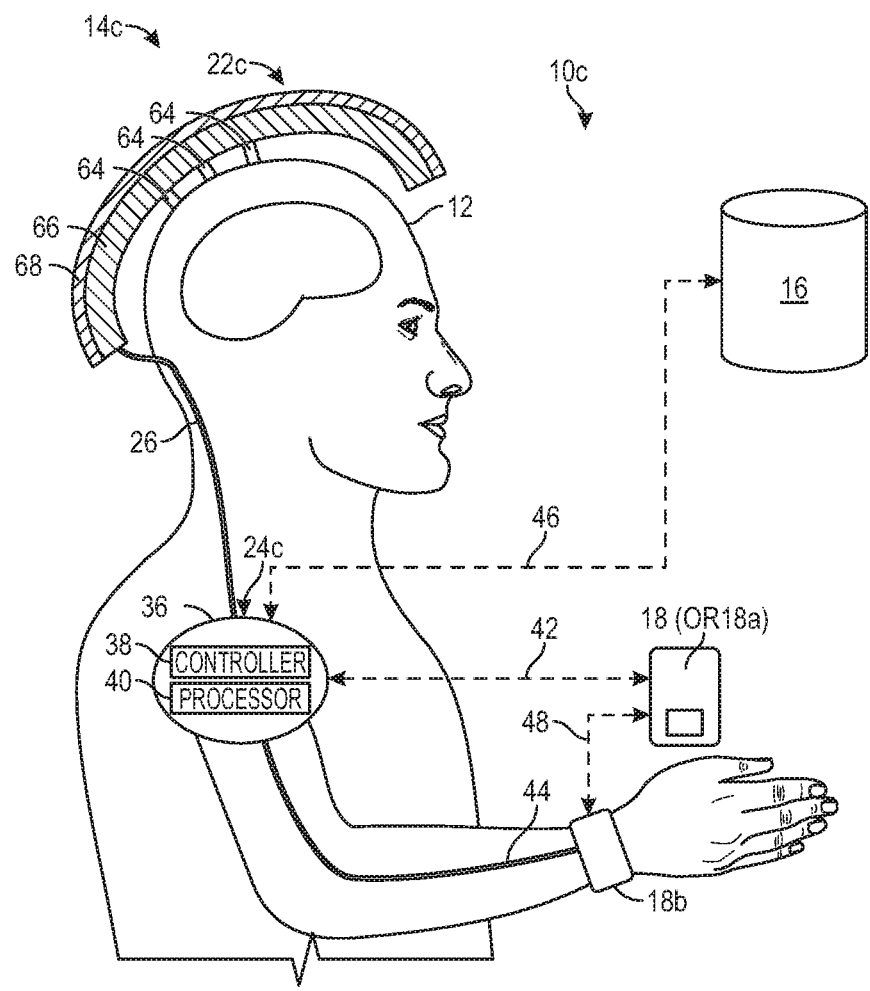
FIG. 7 is a view of still another specific embodiment of the non-invasive anti-priming system of FIGS. 1A and 1B.

Referring to FIG. 7, still another particular embodiment of an anti-priming system 10c will now be described. The non-invasive anti-priming system 10c comprises a magnetically-based non-invasive brain interface assembly 14c, which may, e.g., incorporate any one or more of the neural activity detection technologies described in U.S. patent application Ser. No. 16,428,871, entitled "Magnetic Field Measurement Systems and Methods of Making and Using," U.S. patent application Ser. No. 16/418,478, entitled "Magnetic Field Measurement System and Method of Using Variable Dynamic Range Optical Magnetometers", U.S. patent application Ser. No. 16/418,500, entitled, "Integrated Gas Cell and Optical Components for Atomic Magnetometry and Methods for Making and Using," U.S. patent application Ser. No. 16/457,655, entitled "Magnetic Field Shaping Components for Magnetic Field Measurement Systems and Methods for Making and Using," U.S. patent application Ser. No. 16/213,980, entitled "Systems and Methods Including Multi-Mode Operation of Optically Pumped Magnetometer(S)," (now U.S. Pat. No. 10,627, 460), U.S. patent application Ser. No. 16/456,975, entitled "Dynamic Magnetic Shielding and Beamforming Using Ferrofluid for Compact Magnetoencephalography (MEG)," U.S. patent application Ser. No. 16/752,393, entitled "Neural Feedback Loop Filters for Enhanced Dynamic Range Magnetoencephalography (MEG) Systems and Methods," U.S. patent application Ser. No. 16/741,593, entitled "Magnetic Field Measurement System with Amplitude-Selective Magnetic Shield," U.S. Provisional Patent Application Ser. No. 62/858,636, entitled "Integrated Magnetometer Arrays for Magnetoencephalography (MEG) Detection Systems and Methods," U.S. Provisional Patent Application Ser. No. 62/836,421, entitled "Systems and Methods for Suppression of Non-Neural Interferences in Magnetoencephalography (MEG) Measurements," U.S. Provisional Patent Application Ser. No. 62/842,818 entitled "Active Shield Arrays for Magnetoencephalography (MEG)," U.S. Provisional Patent Application Ser. No. 62/926,032 entitled "Systems and Methods for Multiplexed or Interleaved Operation of Magnetometers," U.S. Provisional Patent Application Ser. No. 62/896,929 entitled "Systems and Methods having an Optical Magnetometer Array with Beam Splitters," U.S. Provisional Patent Application Ser. No. 62/960,548 entitled "Methods and Systems for Fast Field Zeroing for Magnetoencephalography (MEG)," U.S. Provisional Patent Application Ser. No. 62/967,787 entitled "Single Controller for Wearable Sensor Unit that Includes an Array Of Magnetometers," U.S. Provisional Patent Application Ser. No. 62/967, 797 entitled "Systems and Methods for Measuring Current Output By a Photodetector of a Wearable Sensor Unit that Includes One or More Magnetometers," U.S. Provisional Patent Application Ser. No. 62/967,803 entitled "Interface Configurations for a Wearable Sensor Unit that Includes One or More Magnetometers," U.S. Provisional Patent Application Ser. No. 62/967,804 entitled "Systems and Methods for Concentrating Alkali Metal Within a Vapor Cell of a Magnetometer Away from a Transit Path of Light," U.S. Provisional Patent Application Ser. No. 62/967,813 entitled "Magnetic Field Generator for a Magnetic Field Measurement System," U.S. Provisional Patent Application Ser. No. 62/967,818 entitled "Magnetic Field Generator for a Magnetic Field Measurement System," U.S. Provisional Patent Application Ser. No. 62/967,823 entitled "Magnetic Field Measurement Systems Including a Plurality of Wearable Sensor Units Having a Magnetic Field Generator," U.S. Provisional Patent Application Ser. No. 62/975,709 entitled "Self-Calibration of Flux Gate Offset and Gain Drift To Improve Measurement Accuracy of Magnetic Fields from the Brain Using a Wearable System," U.S. Provisional Patent Application Ser. No. 62/975,693 entitled "Nested and Parallel Feedback Control Loops for Ultra-Fine Measurements of Magnetic Fields from the Brain Using a Wearable MEG System," U.S. Provisional Patent Application Ser. No. 62/975,719 entitled "Estimating the Magnetic Field at Distances from Direct Measurements to Enable Fine Sensors to Measure the Magnetic Field from the Brain Using a Wearable System," U.S. Provisional Patent Application Ser. No. 62/975,723 entitled "Algorithms that Exploit Maxwell's Equations and Geometry to Reduce Noise for Ultra-Fine Measurements of Magnetic Fields from the Brain Using a Wearable MEG System," U.S. Provisional Patent Application Ser. No. 62/975,727 entitled "Optimal Methods to Feedback Control and Estimate Magnetic Fields to Enable a Wearable System to Measure Magnetic Fields from the Brain," and U.S. Provisional Patent Application Ser. No. 62/983,406 entitled "Two Level Magnetic Shielding of Magnetometers," which are all expressly incorporated herein by reference.

The brain interface assembly 14c includes a magnetoencephalography (MEG) head-worn unit 22c that is configured for being applied to the user 12, and in this case, worn on the head of the user 12; and an auxiliary non-head-worn unit 24c (e.g., worn on the neck, shoulders, chest, or arm). Alternatively, the functionality of the unit 24c may be incorporated into the head-worn unit 22c, as described below. The auxiliary non-head-worn unit 24c may be coupled to the head-worn unit 22c via a wired connection 26 (e.g., electrical wires). Alternatively, the brain interface assembly 14c may use a non-wired connection (e.g., wireless radio frequency (RF) signals (e.g., Bluetooth, Wifi, cellular, etc.) or optical links (e.g., fiber optic or infrared (IR)) for providing power to or communicating between the respective head-worn unit 22c and the auxiliary unit 24c.

The head-worn unit 22c includes a plurality of optically pumped magnetometers (OPMs) 64 or other suitable magnetometers to measure biologically generated magnetic fields from the brain of the user 12 and a passive shield 66 (and/or flux concentrators). By placing the passive shield 66 over the head of the user 12, the ambient background magnetic field arising from areas outside the passive shield 66 is greatly decreased and the magnetometers 64 can measure or detect magnetic fields from activity occurring in the brain of the user 12 due to the reduction in the ambient background magnetic field.

An OPM is an optical magnetometry system used to detect a magnetic field that propagates through the human head. Optical magnetometry can include the use of optical methods to measure a magnetic field with very high accuracy—on the order of $1 \times 10^{-15}$ Tesla. Of particular interest for their high-sensitivity, an OPM can be used in optical magnetometry to measure weak magnetic fields. (The Earth's magnetic field is typically around 50 micro Tesla). In at least some systems, the OPM has an alkali vapor gas cell that contains alkali metal atoms in a combination of gas, liquid, or solid states (depending on temperature). The gas cell may contain a quenching gas, buffer gas, or specialized anti-relaxation coatings or any combination thereof. The size of the gas cells can vary from a fraction of a millimeter up to several centimeters, allowing the practicality of OPMs to be used with wearable non-invasive brain interface devices.

The head-worn unit 22c further comprises a support housing structure 68 containing the OPMs 64, passive shield 66, and other electronic or magnetic components. As will be described in further detail below, the support housing structure 84 may be shaped, e.g., have a banana, headband, cap, helmet, beanie, other hat shape, or other shape adjustable and conformable to the user's head, such that the OPMs 64 are in close contact with the outer skin of the head, and in this case, the scalp of the user 12. The support housing structure 68 may be made out of any suitable cloth, soft polymer, plastic, hard shell, and/or any other suitable material as may serve a particular implementation.

The auxiliary unit 24c comprises the housing 36 containing the controller 38 and the processor 40. The controller 38 is configured for controlling the operational functions of the head-worn unit 22c, whereas the processor 40 is configured for processing the magnetic fields detected by the head-worn unit 22c to detect and localize the neural activity within the brain of the user 12. The auxiliary unit 24c may additionally include a power supply (which if head-worn, may take the form of a rechargeable or non-chargeable battery), a control panel with input/output functions, a display, and memory. Alternatively, power may be provided to the auxiliary unit 24c wirelessly (e.g., by induction).

The functionalities of the database, server, or cloud structure 16 and biofeedback assembly 18 (or 18') may be the same as described above with respect to FIGS. 1A and 1B.

The biofeedback assembly 18 (or the non-wearable peripheral biofeedback device 18a of the biofeedback assembly 18') is coupled to the auxiliary unit 24c of the brain interface assembly 14c via a wireless connection 42 (e.g., wireless radio frequency (RF) signals (e.g., Bluetooth, Wifi, cellular, etc.) or optical links (e.g., fiber optic or infrared (IR)) for communicating between the biofeedback assembly 18 and the brain interface assembly 14c (and/or the biofeedback assembly 18). Alternatively, a wired connection between the biofeedback assembly 18 (or the non-wearable peripheral biofeedback device 18a of the biofeedback assembly 18') and the brain interface assembly 14c may be used.

The wearable biofeedback device 18b of the alternative biofeedback assembly 18' is coupled to the brain interface assembly 14c (and in this case, to the auxiliary unit 24c) via a wired connection 44 (e.g., electrical wires). Alternatively, a non-wired connection (e.g., wireless radio frequency (RF) signals (e.g., Bluetooth, Wifi, cellular, etc.) or optical links (e.g., fiber optic or infrared (IR)) for providing power to or communicating between the respective the auxiliary unit 24c of the brain interface assembly 14c and the wearable biofeedback device 18b of the alternative biofeedback assembly 18' may be used. The non-wearable peripheral biofeedback device 18a and wearable biofeedback device 18b of the alternative biofeedback assembly 18' may be coupled to each other via a wired connection (e.g., electrical wires) or a non-wired connection 48 (e.g., wireless radio frequency (RF) signals (e.g., Bluetooth, Wifi, cellular, etc.) or optical links (e.g., fiber optic or infrared (IR)), for providing power to or communicating therebetween.

The database, server, or cloud structure 16 may be coupled to the auxiliary unit 24c of the brain interface assembly 14c (and/or the biofeedback assembly 18 (or 18')) via a wireless connection 46 (e.g., wireless radio frequency (RF) signals (e.g., Bluetooth, Wifi, cellular, etc.) or optical links (e.g., fiber optic or infrared (IR)) for providing power to or communicating between the biofeedback assembly 18 (or 18') and the database, server or cloud structure 16. Alternatively, a wired connection between the database, server, or cloud structure 16 and the auxiliary unit 24c of the brain interface assembly 14c (and/or the biofeedback assembly 18 (or 18')) may be used.

Figure 8A:
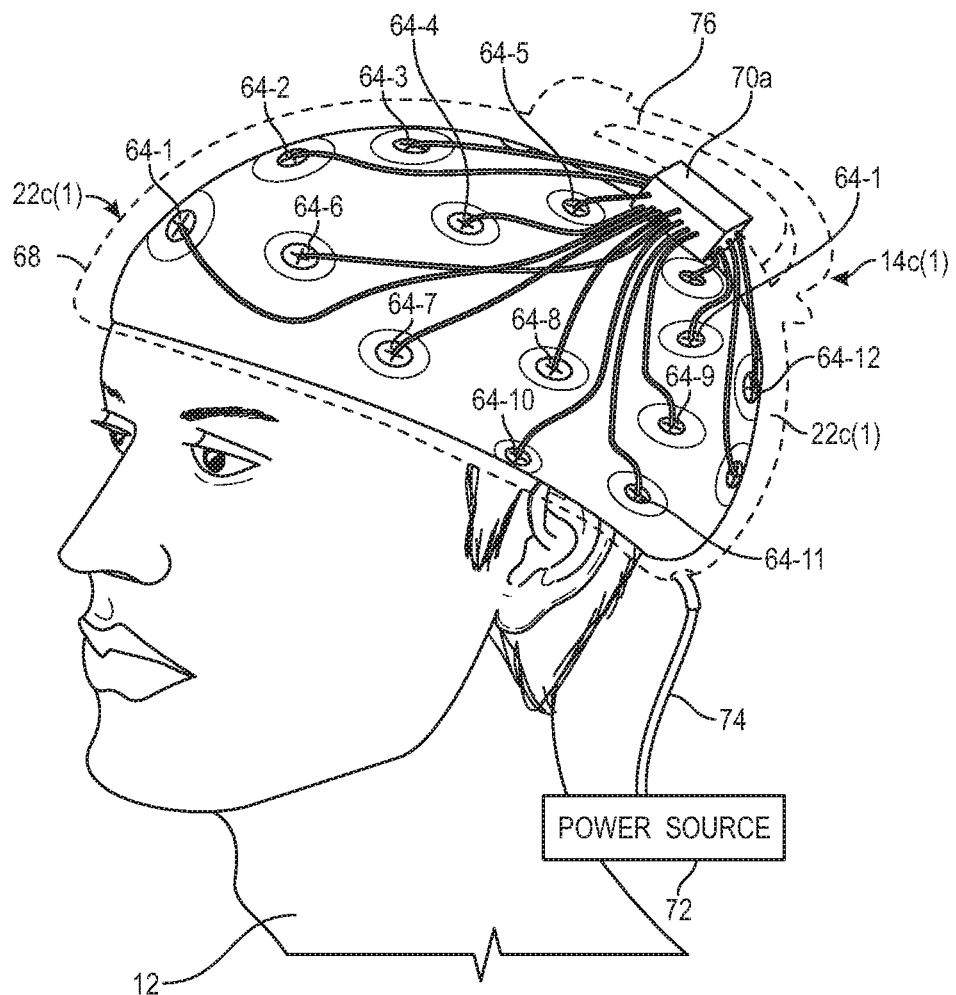
FIG. 8A-8C illustrate exemplary non-invasive wearable devices as used with the system of FIG. 7.
Figure 8B:
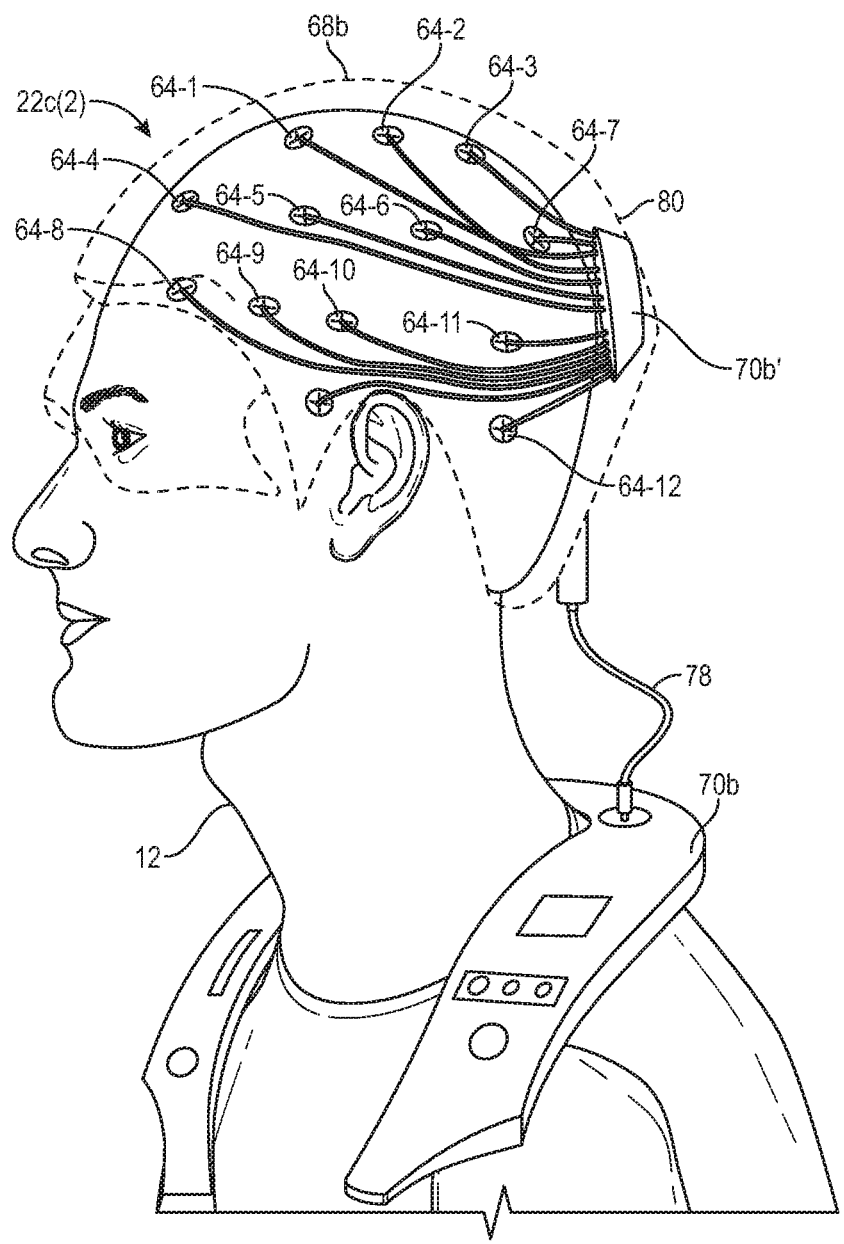
Figure 8C:
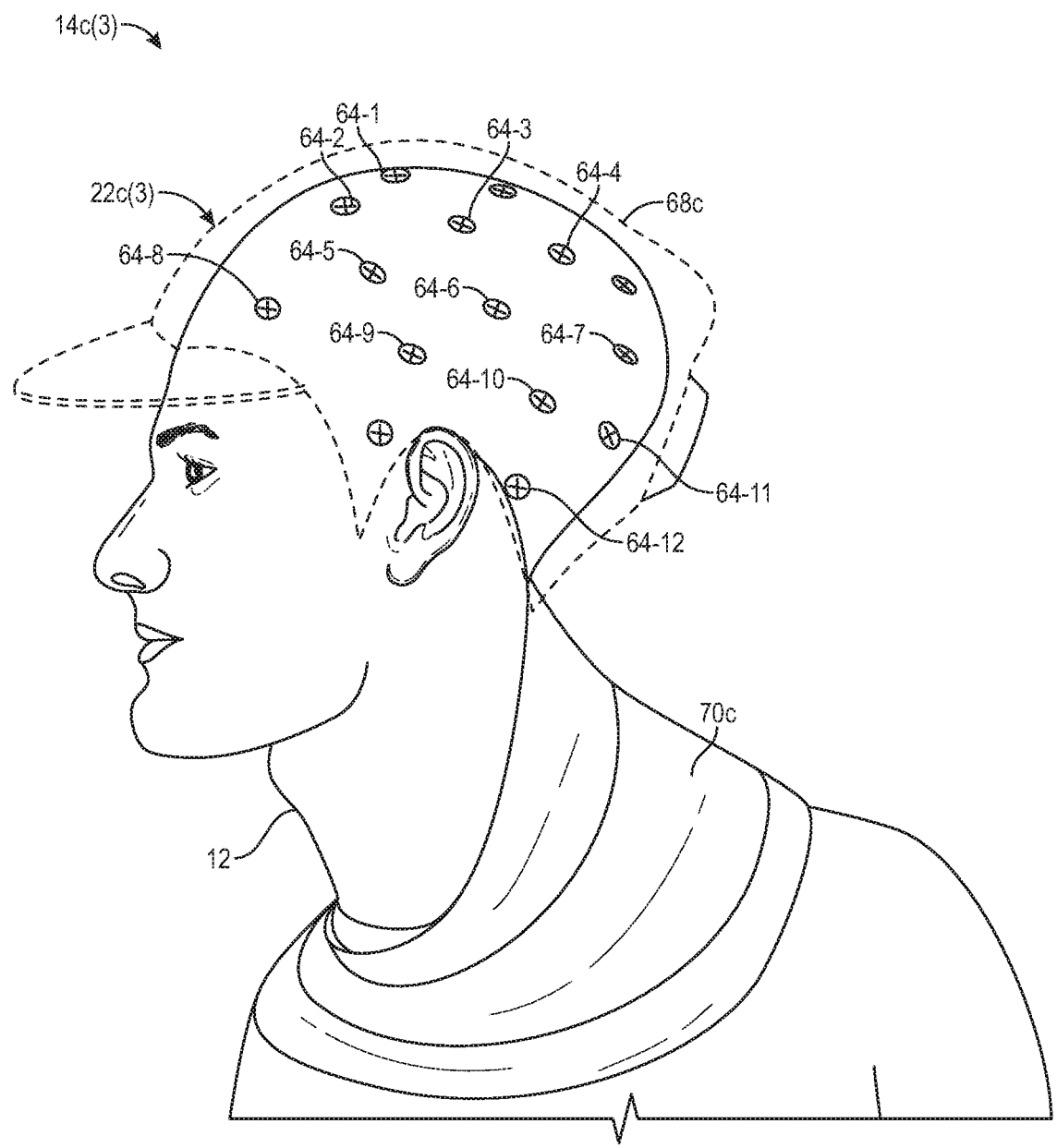

Referring now to FIGS. 8A-8C, different embodiments of the brain interface assembly 14c will be described. Such brain interface assemblies 14c may communicate wirelessly or via wire with the biofeedback assembly 18 (or 18'), and database, server, cloud structure 16, as described above. Each of the brain interface assemblies 14c described below comprises a head-worn unit 22c having a plurality of OPMs 64, a passive shield 66, and a support housing structure 68 in which the OPMs 64 and passive shield 66 are embedded. Each of brain interface assemblies 14c may also comprise a control/processing unit 70 for controlling the operational functions of the OPMs 64, and processing the magnetic fields detected by the OPMs 64 to detect and localize the neural activity within the brain of the user 12. As will be described in further detail below, the control/processing unit 70 may be contained in the head-worn unit 22c or may be incorporated into a self-contained auxiliary unit. As will be set forth below, the support housing structure 68 may be shaped, e.g., have a banana, headband, cap, helmet, beanie, other hat shape, or other shape adjustable and conformable to the user's head, such that the magnetometers 64 are in close contact with the outer skin of the head, and in this case, the scalp of the user 12.

As shown in FIG. 8A, a brain interface assembly 14c(1) comprises a head-worn unit 22c(1) and a power source 72 coupled to the head-worn unit 22c(1) via a wired connection 74. The head-worn unit 22c(1) includes the OPMs 64 (shown as 64-1 through 64-12) and a control/processing unit 70a. The head-worn unit 22c(1) further includes a support housing structure 68a that takes a form of a helmet that contains the OPMs 64, passive shield 66, and control/processing unit 70a. The material for the helmet 68a may be selected out of any suitable cloth, soft polymer, plastic, hard shell, and/or any other suitable material as may serve a particular implementation. The power source 72 may be implemented by a battery and/or any other type of power source configured to provide operating power to the magnetometers 64, control/processing unit 70a, and any other component included within the brain interface assembly 22c(1) via the wired connection 74. The head-worn unit 22c(1) optionally includes a handle 76 affixed to the helmet 68a for providing a convenient means of carrying the head-worn unit 22c(1).

As shown in FIG. 8B, a brain interface assembly 14c(2) comprises a head-worn unit 22c(2) and a control/processing unit 70b coupled to the head-worn unit 22b(2) via a wired connection 78. The head-worn unit 22c(2) includes the OPMs 64 (shown as 64-1 through 64-12), and a support housing structure 68b that takes a form of a helmet that contains the OPMs 64 and passive shield 66. The material for the helmet 68b may be selected out of any suitable cloth, soft polymer, plastic, hard shell, and/or any other suitable material as may serve a particular implementation. Unlike the control/processing unit 70*a* of the brain interface assembly 14*c*(1) illustrated in FIG. 8A, which is contained in the head-worn unit 22*c*(1), the control/processing unit 70*b* is self-contained, and may take the form of a garment (e.g., a vest, partial vest, or harness) for being worn on the shoulders of the user 12. The self-contained control/processing unit 70*b* may additionally include a power supply (which if head-worn, may take the form of a rechargeable or non-chargeable battery), a control panel with input/output functions, a display, and memory. Alternatively, power may be provided to the self-contained control/processing unit 70*b* wirelessly (e.g., by induction). The head-worn unit 22*c*(2) optionally includes a crest or other protrusion 80 formed in the helmet 68*b* for providing means of carrying a control/processing unit 70*b'*.

As shown in FIG. 8C, a brain interface assembly 14*c*(3) comprises a head-worn unit 22*c*(3) and a control/processing unit 70*c*. The head-worn unit 22*c*(3) includes the OPMs 64 (shown as 64-1 through 64-12), and a support housing structure 68*c* that takes a form of a baseball cap that contains the OPMs 64 and passive shield 66. The material for baseball cap 68*c* may be selected out of any suitable cloth, soft polymer, plastic, hard shell, and/or any other suitable material as may serve a particular implementation. The control/processing unit 70*c* is self-contained, and may take the form of a garment (e.g., scarf) for being worn around the neck of the user 12. The self-contained control/processing unit 70*c* may additionally include a power supply (which if head-worn, may take the form of a rechargeable or non-chargeable battery), a control panel with input/output functions, a display, and memory. Alternatively, power may be provided to the self-contained control/processing unit 70*c* wirelessly (e.g., by induction).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A non-invasive anti-priming system, comprising:
   a biofeedback assembly configured for providing a list of training sessions to a user corresponding to a desired mental state;
   a non-invasive brain interface assembly configured for detecting brain activity of a user while the biofeedback assembly provides a tagged training session in the training session list to the user; and
   at least one processor configured for determining a mental state of the user based on the detected brain activity,
   wherein, if the determined mental state matches the desired mental state, the at least processor is configured for automatically modifying the training session list to retain the tagged training session in the training session list; and
   wherein, if the determined mental state does not match the desired mental state, the at least processor is configured for automatically modifying the training session list to discard the tagged training session from the training session list.

2. The non-invasive anti-priming system of claim 1, wherein the non-invasive brain interface assembly is further configured for detecting brain activity of a user when the user is exposed to an external stimulus, wherein the at least one processor is further configured for determining that the user is being negatively primed by the external based on the detected brain activity, and wherein the biofeedback assembly is further configured for automatically providing the tagged training session to the user that promotes a positive mental state of the user in response to the at least one processor determining that the user is being negatively primed by the external stimulus.

3. The non-invasive anti-priming system of claim 2, wherein the external stimulus comprises one of an advertisement, social or political message, or a sales tactic.

4. The non-invasive anti-priming system of claim 2, wherein the at least one processor is configured for determining that the user is being negatively primed by the external stimulus by determining that the user has a negative mental state based on the detected brain activity.

5. The non-invasive anti-priming system of claim 4, wherein the negative mental state is one of anxiety or fear.

6. The non-invasive anti-priming system of claim 2, wherein the biofeedback assembly is further configured for automatically providing an alert that the user is being negatively primed by the external stimulus.

7. The non-invasive anti-priming system of claim 6, wherein the biofeedback assembly comprises a wearable feedback device configured for automatically providing the alert to the user.

8. The non-invasive anti-priming system of claim 2, wherein the positive mental state is one of joy, relaxation, and a cognitive state.

9. The non-invasive anti-priming system of claim 2, wherein the tagged training session comprises instructional media promoting the positive mental state of the user.

10. The non-invasive anti-priming system of claim 2, wherein the tagged training session comprises a mental exercise administered to the user to promote the positive mental state of the user.

11. The non-invasive anti-priming system of claim 2, wherein the biofeedback assembly comprises a non-wearable peripheral feedback device configured for automatically providing the tagged training session to the user.

12. The non-invasive anti-priming system of claim 1,
   wherein, if the determined mental state matches the desired mental state, the at least processor is configured for automatically modifying the training session list to include more training sessions in the training session list having the same attributes as the tagged training session; and
   wherein, if the determined mental state does not match the desired mental state, the at least processor is configured for automatically modifying the training session list to include less training sessions in the training session list having the same attributes as the tagged training session.

13. The non-invasive anti-priming system of claim 1, wherein the desired mental state is a positive mental state.

14. The non-invasive anti-priming system of claim 13, wherein the positive mental state comprises one of joy, relaxation, and a cognitive state.

15. The non-invasive anti-priming system of claim 1, wherein the training session comprises instructional media promoting a positive mental state of the user.

16. The non-invasive anti-priming system of claim 1, wherein the training session comprises a mental exercise administered to the user to promote a positive mental state of the user.

17. A method of correcting negative priming of a user, comprising:
    providing a tagged training session in a list of training sessions to the user corresponding to a desired mental state of the user;
    detecting brain activity of the user using a non-invasive brain interface while the tagged training session is provided to the user;
    determining a mental state of the user based on the detected brain activity; and
    automatically modifying the training session list to retain the tagged training session in the training session list if the determined mental state matches the desired mental state; and
    automatically modifying the training session list to discard the tagged training session from the training session list if the determined mental state does not match the desired mental state.

18. The method of claim 17, further comprising:
    detecting brain activity of the user using the non-invasive brain interface when the user is exposed to an external stimulus;
    determining that the user is being negatively primed by the external stimulus based on the detected brain activity; and
    automatically providing the tagged training session to the user that promotes a positive mental state of the user in response to determining that the user is being negatively primed by the external stimulus.

19. The method of claim 18, wherein the external stimulus comprises one of an advertisement, social or political message, or a sales tactic.

20. The method of claim 18, wherein determining that the user is being negatively primed by the external stimulus comprises determining that the user has a negative mental state based on the detected brain activity.

21. The method of claim 20, wherein the negative mental state is one of anxiety or fear.

22. The method of claim 18, wherein the positive mental state is one of joy, relaxation, and a cognitive state.

23. The method of claim 18, wherein the tagged training session comprises instructional media promoting the positive mental state of the user.

24. The method of claim 18, wherein the tagged training session comprises a mental exercise administered to the user to promote the positive mental state of the user.

25. The method of claim 18, further comprising automatically providing an alert that the user is being negatively primed by the external stimulus.

26. The method of claim 17,
    wherein, if the determined mental state matches the desired mental state, the training session list is automatically modified to include more training sessions in the training session list having the same attributes as the tagged training session; and
    wherein, if the determined mental state does not match the desired mental state, the training session list is automatically modified to include less training sessions in the training session list having the same attributes as the tagged training session.

27. The method of claim 17, wherein the desired mental state is a positive mental state.

28. The method of claim 27, wherein the positive mental state comprises one of joy, relaxation, and a cognitive state.

29. The method of claim 17, wherein the tagged training session comprises instructional media promoting a positive mental state of the user.

30. The method of claim 17, wherein the tagged training session comprises a mental exercise administered to the user to promote a positive mental state of the user.

* * * * *